(12) United States Patent
Wang et al.

(10) Patent No.: US 8,673,567 B2
(45) Date of Patent: Mar. 18, 2014

(54) METHOD AND KIT FOR NUCLEIC ACID SEQUENCE DETECTION

(75) Inventors: Youxiang Wang, Palo Alto, CA (US); Wenjing Tao, Hercules, CA (US)

(73) Assignee: Atila Biosystems, Inc., Palo Alto, CA (US)

( * ) Notice: Subject to any disclaimer, the term of this patent is extended or adjusted under 35 U.S.C. 154(b) by 687 days.

(21) Appl. No.: 11/715,636

(22) Filed: Mar. 8, 2007

(65) Prior Publication Data

US 2007/0269825 A1    Nov. 22, 2007

Related U.S. Application Data

(60) Provisional application No. 60/780,487, filed on Mar. 8, 2006.

(51) Int. Cl.
*C12Q 1/68* (2006.01)
*C12P 19/34* (2006.01)
*G01N 33/53* (2006.01)
*C07H 21/04* (2006.01)

(52) U.S. Cl.
USPC ......... 435/6.12; 435/6.19; 435/7.1; 435/91.2; 536/24.3

(58) Field of Classification Search
None
See application file for complete search history.

(56) References Cited

U.S. PATENT DOCUMENTS

| | | | |
|---|---|---|---|
| 4,883,750 A | 11/1989 | Whiteley | |
| 4,988,617 A | 1/1991 | Landegren | |
| 5,310,652 A * | 5/1994 | Gelfand et al. | 435/6 |
| 5,494,810 A | 2/1996 | Barany | |
| 5,871,921 A | 2/1999 | Landegren | |
| 6,027,889 A | 2/2000 | Barany | |
| 6,210,884 B1 * | 4/2001 | Lizardi | 435/6.12 |
| 6,344,316 B1 * | 2/2002 | Lockhart et al. | 506/9 |
| 6,355,431 B1 * | 3/2002 | Chee et al. | 435/6 |
| 6,436,635 B1 * | 8/2002 | Fu et al. | 435/7.24 |
| 6,498,023 B1 * | 12/2002 | Abarzua | 435/91.2 |
| 6,537,748 B1 | 3/2003 | Goelet | |
| 6,762,018 B1 * | 7/2004 | Merenkova | 435/6 |
| 6,858,412 B2 | 2/2005 | Davis | |
| 6,890,741 B2 | 5/2005 | Fan | |
| 2003/0165917 A1 * | 9/2003 | Ullman et al. | 435/6 |
| 2004/0191814 A1 * | 9/2004 | Zhou et al. | 435/6 |
| 2006/0078906 A1 | 4/2006 | Chen | |

FOREIGN PATENT DOCUMENTS

WO    WO 9704131 A1 *    2/1997

OTHER PUBLICATIONS

Ahern et al. Biochemical, reagent kits offer scientists good return on investment. The Scientist 1995; vol. 9, 5 pages.*
Veuger et al. A novel RT-PCR-based protein activity truncation assay for direct assessment of deoxycytidine kinase in small numbers of purified leukemic cells. Leukemia (2000) 14(9): 1678-1684.*
Broude et al. DNA microarrays with stem-loop DNA probes: preparation and applications. Nucleic Acids Research (2001) 29(19): e92 (11 printed pages).*
Cleary et al. Production of complex nucleic acid libraries using highly parallel in situ oligonucleotide synthesis. Nature Methods (2004) 1(3): 241-248.*
Polstra et al. Development of real-time NASBA assays with molecular beacon detection to quantify mRNA coding for HHV-8 lytic and latent genes. BMC Infectious Diseases (2002) 2: 18 (10 printed pages).*
Wiltshire et al. Clinical Chemistry (2000) 46(12): 1990-1993.*
Kuhn, Keiko; Frank-Kamenetskii; Maxim D., Template-Independent ligation of single-stranded DNA by T4 DNA ligase, FEBS Journal, 2005, vol. 22, No. 23, p. 5991-6000.
M Nilsson, H Almgren, M Samiotaki, M Kwiatkowsi, and U Landegren, Padlock probes: circularizing oligonucleotides for localized DNA detection, Science, 1994 265: 2085.
Paul Hardenbol, Highly multiplexed molecular inversion probe genotyping: over 10,000 targeted SNPs genotyped in a single tube assay, Genome Research, 2005, 15, 269.
Michael S. Akhras, PathogenMip Assay: A Multiplex Pathogen Detection Assay, PLoS One, 2007, 2(2), e233.
O. K. Kaboev, PCR Hot Start Using Primers with the Structure of Molecular Beacons (hairpin-like structure), Nucleic Acids Research, 2000, vol. 28, No. 21, e94.
Manjit Kaur, Novel amplification of DNA in a hairpin structure: towards a radical elimination of PCR errors from amplified DNA, nucleic acids research, 2003, vol. 31, e26.
David E. Weemmer, Preparation and melting of single strand circular DNA loops, Nucleic acids research, 1985, vol. 13, 8611.

* cited by examiner

Primary Examiner — Angela M Bertagna
(74) Attorney, Agent, or Firm — Alston & Bird LLP

(57) ABSTRACT

A method and kit for detecting the presence of a target sequence in a polynucleotide analyte contained in a sample are disclosed. In practicing the method, the sample is mixed with a single-stranded DNA target probe having a sequence capable of hybridizing with the target sequence, under conditions effective to form a double-stranded complex of the analyte and the single-stranded DNA target probe, and the single-stranded DNA target probe in the complex is reacted in the presence of a polymerase and one to three nucleotide triphosphates, to add a selected one or more target-directed nucleotide bases to single-stranded DNA target probe's 3' end to produce a modified probe. The modified probe is hybridized with a single-stranded DNA detection probe, the two probes are ligated to form a two-probe ligation product, and the presence of the ligation product is detected.

29 Claims, 16 Drawing Sheets

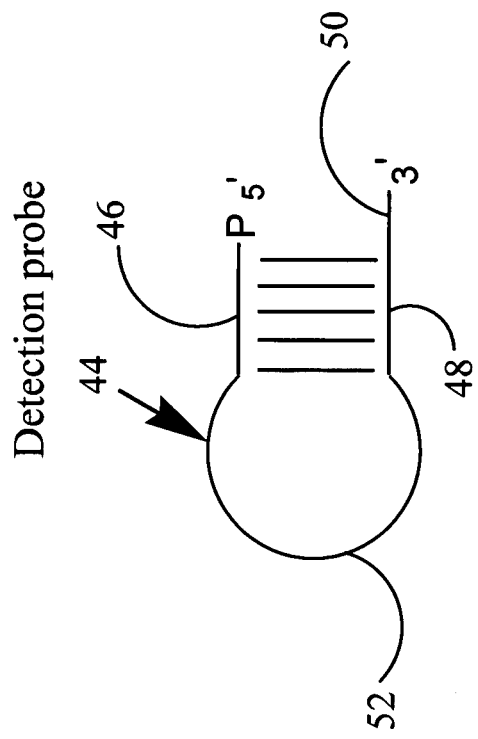
Figure 2 C    Detection probe can be single or double stranded with or without loop structure

```
SEQUENCE LISTING

<160> NUMBER OF SEQ ID NOS: 31

<210> SEQ ID NO 1
<211> LENGTH: 31
<212> TYPE: DNA
<213> ORGANISM: artificial
<220> FEATURE:
<223> OTHER INFORMATION: synthetic sequence

<400> SEQUENCE: 1
ggctccatac ggactcccac agtgaggagc c                              31

<210> SEQ ID NO 2
<211> LENGTH: 30
<212> TYPE: DNA
<213> ORGANISM: artificial
<220> FEATURE:
<223> OTHER INFORMATION: synthetic sequence

<400> SEQUENCE: 2
atcccattat cctccatgca atgggatcca                                30

<210> SEQ ID NO 3
<211> LENGTH: 37
<212> TYPE: DNA
<213> ORGANISM: artificial
<220> FEATURE:
<223> OTHER INFORMATION: synthetic sequence

<400> SEQUENCE: 3
ccgtgtgcta tatgttagta ttggacacac acggcca                        37

<210> SEQ ID NO 4
<211> LENGTH: 51
<212> TYPE: DNA
<213> ORGANISM: artificial
<220> FEATURE:
<223> OTHER INFORMATION: synthetic sequence

<400> SEQUENCE: 4
aatatatgga ggataatggg atccaggctc ctcactgtgg gagaagaagt t         51
```

<210> SEQ ID NO 5
<211> LENGTH: 51
<212> TYPE: DNA
<213> ORGANISM: artificial
<220> FEATURE:
<223> OTHER INFORMATION: synthetic sequence

<400> SEQUENCE: 5
aatatatgga ggataatggg atccacgctc ctcactgtgg gagaagaagt t            51

<210> SEQ ID NO 6
<211> LENGTH: 248
<212> TYPE: DNA
<213> ORGANISM: artificial
<220> FEATURE:
<223> OTHER INFORMATION: synthetic sequence

<400> SEQUENCE: 6
gaacaacgtt aacccatgtt gttttttgtt tctcttatgt gtgtggagcc ttgttgtgct    60
cccctcatgc gtgaggccag ttttgtgtga agatgaaggt tgggatggag tggttgtgac   120
agcatcaaac ctcttagcac ttgaagcttt caagcaagag ttggcttgat ccagaagggt   180
tcttgcggag ctggaatgac agtggctatg gagcttgttc cggaggttgg gttggaatca   240
agtgtgct                                                            248

<210> SEQ ID NO 7
<211> LENGTH: 244
<212> TYPE: DNA
<213> ORGANISM: artificial
<220> FEATURE:
<223> OTHER INFORMATION: synthetic sequence

<400> SEQUENCE: 7
tgatccagaa gggttcttgc ggagctggaa tgacagtggc tatggagctt gttccggagg    60
ttgggttgga atcaagtgtg ctcaagggac aggttattgt gatccagctt ccttggaagg   120
gtttgagggg tcgaatcacc gacaaaattg gccaacttca aggcctcagg aagcttagtc   180
ttcatgataa ccaaattggt ggttcaatcc cttcaacttt gggacttctt cccaacctta   240
gagg                                                                244

<210> SEQ ID NO 8
<211> LENGTH: 248
<212> TYPE: DNA
<213> ORGANISM: artificial
<220> FEATURE:
<223> OTHER INFORMATION: synthetic sequence

<400> SEQUENCE: 8
cctttaccag ctagcctaac tcactcattt tctctcactt ttctttctct tcaaaataac    60
aatctttctg gctcccttcc taactcttgg ggtgggaatt ccaagaatgg cttctttagg   120
cttcaaaatt tgatcctaga tcaataactt tttcactggt gacgttcctg cttctttggg   180
tagcttaaga gagctcaatg agatttccct tagtcataat aagtttagtg gagctatacc   240
aaatgaaa                                                            248

<210> SEQ ID NO 9
<211> LENGTH: 241
<212> TYPE: DNA
<213> ORGANISM: artificial
<220> FEATURE:
<223> OTHER INFORMATION: synthetic sequence -continued

```
<400> SEQUENCE: 9
ctgcttttct gcctgatcag aaagagatca acatctaagg ccgggaacgg ccaagccacc      60
gagggtagag cggtcactta tgaggacaga aaaaggagtc cctccagttg ctggctggtt     120
gatgttgaag caggtgggga ggctggaggg gaactagtcc attttgatgg accaatggct    180
tttacagctg atgatctctt gtgtgcaaca gctgagatca tgggaaagag caccaatgga    240
a                                                                      241

<210> SEQ ID NO 10
<211> LENGTH: 40
<212> TYPE: DNA
<213> ORGANISM: artificial
<220> FEATURE:
<223> OTHER INFORMATION: synthetic sequence

<400> SEQUENCE: 10
ctttcaagca agagttggct gatccagaag ggttcttgcg                             40

<210> SEQ ID NO 11
<211> LENGTH: 35
<212> TYPE: DNA
<213> ORGANISM: artificial
<220> FEATURE:
<223> OTHER INFORMATION: synthetic sequence

<400> SEQUENCE: 11
gatccagaat cttgcgcaag aacccttctg gatca                                  35

<210> SEQ ID NO 12
<211> LENGTH: 47
<212> TYPE: DNA
<213> ORGANISM: artificial
<220> FEATURE:
<223> OTHER INFORMATION: synthetic sequence

<400> SEQUENCE: 12
ccgtgtgcta catctaagta taggactatg ttatattggg cacacgg                     47

<210> SEQ ID NO 13
<211> LENGTH: 41
<212> TYPE: DNA
<213> ORGANISM: artificial
<220> FEATURE:
<223> OTHER INFORMATION: synthetic sequence

<400> SEQUENCE: 13
gttggaatca agtgtgctca gggacaggtt attgtgatcc a                           41

<210> SEQ ID NO 14
<211> LENGTH: 38
<212> TYPE: DNA
<213> ORGANISM: artificial
<220> FEATURE:
<223> OTHER INFORMATION: synthetic sequence

<400> SEQUENCE: 14
gggacaggat cttgcgcgga tcacaataac ctgtccct                               38

<210> SEQ ID NO 15
<211> LENGTH: 49
<212> TYPE: DNA
<213> ORGANISM: artificial
<220> FEATURE:
<223> OTHER INFORMATION: synthetic sequence
```

```
<400> SEQUENCE: 15
ccgtgtgcta catctaagta taggactatg ttatattggg cacacggca              49

<210> SEQ ID NO 16
<211> LENGTH: 38
<212> TYPE: DNA
<213> ORGANISM: artificial
<220> FEATURE:
<223> OTHER INFORMATION: synthetic sequence

<400> SEQUENCE: 16
aatttgatcc tagatcataa cttttttcact ggtgacgt                         38

<210> SEQ ID NO 17
<211> LENGTH: 46
<212> TYPE: DNA
<213> ORGANISM: artificial
<220> FEATURE:
<223> OTHER INFORMATION: synthetic sequence

<400> SEQUENCE: 17 taacttttc acatcttgcg cggcacgtca ccagtgaaaa agttat                  46

<210> SEQ ID NO 18
<211> LENGTH: 39
<212> TYPE: DNA
<213> ORGANISM: artificial
<220> FEATURE:
<223> OTHER INFORMATION: synthetic sequence

<400> SEQUENCE: 18
agtccctcca gttgctgctg gttgatgttg aagcaggtg                         39

<210> SEQ ID NO 19
<211> LENGTH: 41
<212> TYPE: DNA
<213> ORGANISM: artificial
<220> FEATURE:
<223> OTHER INFORMATION: synthetic sequence

<400> SEQUENCE: 19
ggttgatgat cttgcgcggc agcctgcttc aacatcaacc a                      41

<210> SEQ ID NO 20
<211> LENGTH: 18
<212> TYPE: DNA
<213> ORGANISM: artificial
<220> FEATURE:
<223> OTHER INFORMATION: synthetic sequence

<400> SEQUENCE: 20
atgttatatt gggcacac                                                18

<210> SEQ ID NO 21
<211> LENGTH: 15
<212> TYPE: DNA
<213> ORGANISM: artificial
<220> FEATURE:
<223> OTHER INFORMATION: synthetic sequence

<400> SEQUENCE: 21
ccagaagggt tcttg                                                   15

<210> SEQ ID NO 22
<211> LENGTH: 15
<212> TYPE: DNA
```

```
<213> ORGANISM: artificial
<220> FEATURE:
<223> OTHER INFORMATION: synthetic sequence

<400> SEQUENCE: 22
caggttattg tgatc                                                    15

<210> SEQ ID NO 23
<211> LENGTH: 16
<212> TYPE: DNA
<213> ORGANISM: artificial
<220> FEATURE:
<223> OTHER INFORMATION: synthetic sequence

<400> SEQUENCE: 23 cttttcact ggtgac                                                    16

<210> SEQ ID NO 24
<211> LENGTH: 16
<212> TYPE: DNA
<213> ORGANISM: artificial
<220> FEATURE:
<223> OTHER INFORMATION: synthetic sequence

<400> SEQUENCE: 24
gttgatgttg aagcag                                                   16

<210> SEQ ID NO 25
<211> LENGTH: 30
<212> TYPE: RNA
<213> ORGANISM: artificial
<220> FEATURE:
<223> OTHER INFORMATION: synthetic sequence

<400> SEQUENCE: 25
gugcucaggg acagguuauu gugauccagc                                    30

<210> SEQ ID NO 26
<211> LENGTH: 37
<212> TYPE: RNA
<213> ORGANISM: artificial
<220> FEATURE:
<223> OTHER INFORMATION: synthetic sequence

<400> SEQUENCE: 26
cgccugucau ccuccaugcu cgggucccga caggcgu                            37

<210> SEQ ID NO 27
<211> LENGTH: 37
<212> TYPE: RNA
<213> ORGANISM: artificial
<220> FEATURE:
<223> OTHER INFORMATION: synthetic sequence

<400> SEQUENCE: 27
gcaggcgauc cuccaugcgg uaauuugcgc gccugcu                            37

<210> SEQ ID NO 28
<211> LENGTH: 37
<212> TYPE: RNA
<213> ORGANISM: artificial
<220> FEATURE:
<223> OTHER INFORMATION: synthetic sequence

<400> SEQUENCE: 28
gcaggcgauc cuccaugcgg uaauuugcgc gccugcu                            37
```

```
<210> SEQ ID NO 29
<211> LENGTH: 57
<212> TYPE: DNA
<213> ORGANISM: artificial
<220> FEATURE:
<223> OTHER INFORMATION: synthetic sequence

<400> SEQUENCE: 29
ctccctatag tgagtcgtat taatcctcca tgctaatacg actcactata gggagca        57

<210> SEQ ID NO 30
<211> LENGTH: 22
<212> TYPE: DNA
<213> ORGANISM: artificial
<220> FEATURE:
<223> OTHER INFORMATION: synthetic sequence

<400> SEQUENCE: 30
ctccctatag tgagtcgtat ta                                             22

<210> SEQ ID NO 31
<211> LENGTH: 24
<212> TYPE: DNA
<213> ORGANISM: artificial
<220> FEATURE:
<223> OTHER INFORMATION: synthetic sequence

<400> SEQUENCE: 31
taatacgact cactataggg agca                                           24
```

METHOD AND KIT FOR NUCLEIC ACID SEQUENCE DETECTION

CROSS-REFERENCE TO RELATED APPLICATION

This application claims priority to U.S. Ser. No. 60/780,487, filed Mar. 8, 2006, entitled Method and Kit for Nucleic Acid Sequence Detection by inventors Youxiang Wang and Wenjing Tao.

FIELD OF THE INVENTION

The invention relates generally to a method and kit for detecting the presence of one or more polynucleotide sequences in a sample.

BACKGROUND

Identification of nucleic acid sequences is a key diagnostic tool in many fields, including medicine, forensics, food production, animal husbandry, and the like, e.g. Jobling et al., Nature Reviews Genetics, 5: 739-751 (2004); Jo et al., Semin. Oncol., 32: 11-23 (2005); Woo et al., J. Clin. Microbiol., 41: 1996-2001 (2003). For example, DNA amplification technologies have found applications in all of these areas, including applications for viral and bacterial detection, viral load monitoring, detection of rare and/or difficult-to-culture pathogens, rapid detection of bio-terror threats, detection of minimal residual disease in cancer patients, food pathogen testing, blood supply screening, and the like, e.g. Mackay, Clin. Microbiol. Infect., 10: 190-212 (2004); Bernard et al., Clinical Chemistry, 48: 1178-1185 (2002).

Suitable nucleic acid amplification methods include both target amplification and signal amplification and may include, but are not limited to, polymerase chain reaction (PCR), ligation chain reaction (LCR, sometimes referred to as oligonucleotide ligase amplification OLA), cycling probe technology (CPT), strand displacement assay (SDA), Rolling circle amplification (RCA), transcription mediated amplification (TMA), nucleic add sequence based amplification (NASBA), and invasive cleavage technology. All of these methods require either two primers or a single primer to hybridize to a target sequence to initiate the amplification. All of these methods require a primer nucleic acid (including nucleic acid analogs) that is hybridized to a target sequence to form a hybridization complex, and an enzyme is added that in some way modifies the primer to form a modified primer. For example, PCR generally requires two primers, dNTPs and a DNA polymerase; LCR requires two primers that adjacently hybridize to the target sequence and a ligase; CPT requires one cleavable primer and a cleaving enzyme; invasive cleavage requires two primers and a cleavage enzyme. etc.

Despite the advances in nucleic acid amplification techniques that are reflected in such widespread applications, there has been limited achievement in performing these techniques in parallel within the same sample, i.e. in multiplexed assays, where multiple target sequences are simultaneously amplified and detected in the same reaction mixture, e.g. Einifro et al., Clin. Microbiol. Rev., 13: 559-570 (2000); Henegarin et al., Biotechniques, 23: 504-511 (1997). When a multiplex assay involves different priming events for different target sequences, the relative efficiency of these events may vary for different targets. This is due to the stability and structural differences between the various primers used. If the rates of product strand renaturation differ for different targets, the extent of competition with priming events will not be the same for all targets. For reactions involving multiple ligation events, such as LCR, there may be small but significant differences in the relative efficiency of ligation events for each target sequence. Since the ligation events are repeated many times, this effect is magnified. For reactions involving reverse transcription (3SR, NASBA) or klenow strand displacement (SDA), the extent of polymerization processivity may differ among different target sequences. For assays involving different replicatable RNA probes, the replication efficiency of each probe is usually not the same, and hence the probes compete unequally in replication reactions catalyzed by Q.beta. replicase. Accordingly, there is a need for amplification methods that are less likely to produce variable and possibly erroneous signal yields in multiplex assays.

Microarray technology has provided an alternative approach for making simultaneous measurements on samples containing multiple polynucleotide analytes, e.g. U.S. Pat. No. 5,700,637, Wang et al., Proc. Nat. Acad. Sci., 99: 15687-15692 (2002); however, such technology has found limited use outside of research laboratories. Furthermore, this technology follows the dominant approach in multiplexed analysis which is to obtain data on every analyte of interest present in the sample. As such, multiplexed assays are primarily concerned with resolving and distinguishing among the plurality of analytes targeted. The number of targets is generally limited in some manner by either the recognition event (e.g. specificity of a probe for a target; the difficulty in designing primer sets that do not interact to negatively effect the amplification) or the detection method (e.g. broad absorption or emission profiles of a chromophore or lumophore limit the number of such labels that can be independently determined). Nonetheless, much work in the field is directed to improving the multiplex capabilities of existing methods by being able to detect or resolve more analytes within a single process.

More recently, several highly multiplexed and ultra-high-throughput genotyping systems have become generally available (Matsuzaki, et al., Nat. Methods 1: 109-111 (2004), Hardenbol, et al., Genome Res. 15: 269-275 (2005), Murray, S. S., et al., Nat. Methods, 1: 113-117 (2004)). However, most of these systems are not flexible due to probe length limitation, and still have limited multiplicity in sample processing due to interprobe hybridization. Therefore, there is a need for developing of sensitive and precise nucleic acid detection methods with high multiplicity.

SUMMARY OF THE INVENTION

The present invention provides methods that are useful and applicable in nucleic acid amplification, nucleic acid detection and protein analysis. The invention includes, in one aspect, a method of detecting the presence of a target sequence in a polynucleotide analyte contained in a sample. The method steps include:

(a) mixing the sample with a target probe having a sequence capable of hybridizing with the target sequence, under conditions effective to form a double-stranded complex of the analyte and the probe, (b) reacting the probe in the complex in the presence of a polymerase and a selected one to three of four possible nucleotide triphosphates, thereby to add a selected one or more target-directed nucleotide bases to the probe's 3' end to produce a modified probe, (c) hybridizing the modified probe with a detection probe, where the detection probe does not hybridize to the target and at least one of the two probes has a sticky end having single strand region complementary to the other probe's single strand region from the end, (d) by the reacting ligating the modified probe with the detection probe to form a two-probe ligation product, and (e) detecting the presence of the ligation product.

In one embodiment, step (b) may optionally include dissociating the modified probe from the target by denaturation or degrading the target.

In one embodiment, the target probe may has a sticky end before or after polymerization reaction in step (b). In another aspect, the complementary portion of one probe's sticky end's single strand sequence to the other probe's single strand sequence at its 3' end or 5' end in (c) may include one or more than one base-pairs.

In one embodiment, ligation modified probe and detection probe in (d) includes enzymatic reaction and chemical reaction.

In one embodiment, the target probe in (a) may include arbitrary sequences that is not complementary to target sequences. The arbitrary sequences may include universal priming site, promote site, cleavage site, non-natural nucleotides, restriction enzyme site, etc.

In another embodiment, the target probe may be a single stranded polynucleotides with a hairpin structure or a double stranded polynucleotides. One end of the double stranded target probe may be connected through covalent bond. The other end of double stranded target probe may be a sticky end before or after adding nucleotide triphosphate in step (b). A sticky end's single strand region may include one or more than one nucleotides.

In one embodiment, the detection probe in (c) may include arbitrary sequences. The arbitrary sequences may include universal priming site, promote site, cleavage site, non-natural nucleotides, restriction enzyme site, etc.

In another embodiment, the detection probe in (c) may be a single stranded polynucleotides with a hairpin structure or a double stranded polynucleotides. One end of the double stranded detection probe may be connected through covalent bond. The other end of double stranded detection probe may be a sticky end. The single strand region of the sticky end may include one or more than one nucleotides.

In one embodiment, polymerase in step (b) may include DNA dependent DNA polymerases or RNA dependent DNA polymerases.

In one embodiment, reaction steps (a)-(e) may be carried out by addition of the components required in the steps to a single reaction vessel, and carrying out the steps under substantially isothermal conditions.

In one embodiment, the amount of target probe in step (a) is in substantial molar excess of the amount of target analyte, and the method may further include repeating steps (a) and (b) to increase the number of modified probes present in the sample. Repeating steps (a) and (b) may include heating the sample after each step (b) to release modified probe from the target polynucleotide, and cooling the sample as part of each step (a) to hybridize unreacted target probe with the target sequence.

In one embodiment, the present invention provides methods for use in detecting a small target region of interest, e.g., a region of 1-6 bases, such as a SNP or known-location point mutation, the target probe may have a 3'-end nucleotide base that is partially complementary to or immediately adjacent the target region of interest, and step (b) may be carried out so the 3'-end sequence of the modified probe is complementary to the target region of interest. In this embodiment, step (b) may be carried out with the addition of a single nucleotide triphosphate.

In one embodiment, the present invention provides methods for use in detecting a plurality of target sequences of interest in one or more polynucleotides in a sample, the sample may be mixed with a plurality of target probes, each is a single-stranded polynucleotides having a hairpin loop structure capable of forming a double-stranded complex with a region of a sample polynucleotide. Here step (a) of the method may include dividing the sample into two or more sample aliquots and mixing each sample aliquot with the plurality of target probes, step (b) may include reacting each sample aliquot with a selected one to three of four different nucleotide triphosphates, a different combination of one to three of four nucleotide triphosphate for each aliquot, and step (c) may include hybridizing the modified probe with an aliquot-specific detection probe, step (d) may include reacting the modified probe with an aliquote-specific detection probe to form ligation products, step (e) may include amplification of the ligation products in each aliquote before detection. Detection plurality of ligation products may include incorporation specific labels in each aliquote during amplification. Amplification methods may include polymerase chain reaction, rolling circle amplification, and transcription. The amplified products may be chemically or enzymatically treated before detection. In another aspect, amplification products from each aliquote may or may not be mixed prior to detection by hybridizing with probes attached on solid surfaces such as array.

In one embodiment, a mixture of plurality of target probes may be synthesized from solid surface in a reaction vessel. Releasing the plurality of target probe from solid surface forms a mixture of plurality of target probes. The mixture of plurality of target probes may be used for detecting a plurality of target sequences of interest in one or more polynucleotides in a sample.

In one embodiment, the present invention provides another methods for use in detecting a plurality of target sequences of interest in one or more polynucleotides in a sample, the sample may be mixed with a plurality of target probes, each is a single-stranded polynucleotides having a hairpin loop structure capable of forming a double-stranded complex with a region of a sample polynucleotide. Here step (e) of the method may include dividing the ligation products into two or more aliquots and amplify each aliquot with specific primers before detection. Amplification methods may include polymerase chain reaction, rolling circle amplification if ligated products are circular. The amplified products may be chemically or enzymatically treated before detection. Alternatively, step (e) of the method may include transcription of the plurality of ligation products and detection of the transcripts by hybridization with probes on solid surface.

In one embodiment, both the detection probe and the modified probe may be single-stranded polynucleotides with hairpin loop structure and may have sticky ends that are complementary to each other, such that two-probe ligation product formed in step (d) is a circular polynucleotides. In a further embodiment, the method in step (d) may include exonuclease treatment of the ligation products. In another further aspect, the circular ligation products may be cleaved before amplification and detection.

In another embodiment, step (e) for detecting the presence of the ligation product may include using the ligation product as a template for the synthesis of a detectable polynucleotide compound. For example, the ligation product may be amplified and detected by PCR, rolling circle amplification (RCA), or by using the ligation product as a source of target-specific transcripts. In one aspect, target-specific transcripts may be produced by initiating from promoter sequences included in the ligation products or by initiating from loop sequences present in the ligation products.

In one embodiment, one of the target or detection probes may be attached to a solid support, so that the ligation product produced in step (d) also becomes attached to the solid support. Step (e) of detecting the presence of the ligation product may include detecting the presence of the ligation product on the support.

In one embodiment, the method may be used, for in a protein-binding assay, where the polynucleotide analyte is carried on a protein-binding agent.

In one embodiment, the present invention provides methods for use in detecting a plurality of protein analytes in protein-binding assay in a sample, the sample may be mixed with a plurality of protein-binding agents, each protein-binding agent carries on a distinguishable polynucleotide sequences. Here step (a) of the method may include a plurality of target probes, each is a single stranded polynucleotides having a hairpin loop structure capable of forming a double-stranded complex with polynucleotide sequences attached on binding agents. Here step (e) of the method may include dividing the ligation products into two or more aliquots and amplify each aliquot with specific primers before detection. Amplification methods may include polymerase chain reaction, rolling circle amplification if ligation products are circular. The amplified products may be chemically or enzymatically treated before detection. In another embodiment, amplification products may be detected by hybridization with detection probes attached on solid surface such as array. In a further embodiment, one of the target probe and detection probe may be attached on solid surface.

In one embodiment, the method may be used for detecting a target nucleic acid molecules from cell lysate. Step (a) may include hybridizing target probe with target nucleic acid molecules in the cell lysate.

In one embodiment, the present invention provides methods for use in detecting an RNA polynucleotide analyte, step (a) of the method may include mixing the sample with a target probe, step (b) may include reacting the probe in the complex in the presence of a reverse transcriptase polymerase to generate a modified probe, and step (c) may include hybridizing the modified probe with a detection probe, and step (d) in the presence of a ligase, ligating the modified probe with the detection probe to form a two-probe ligation product. Reaction steps (a)-(e) may be carried out by sequential addition of the components required in the steps to a single reaction vessel, and carrying out the steps under substantially isothermal conditions. The detection probe may include a promoter region, such that the ligation product produced in step (d) places a target-probe sequence under the control of the promoter region, and step (e) includes reacting the two-probe ligation product with a promoter-dependent polymerase under conditions effective to promote synthesis of transcripts containing the target-probe complementary sequence, and detecting the presence of the transcripts. The presence of the transcripts may be detected in step (e) by reacting the transcripts with molecular beacon probes contained in the reaction medium used to generate the transcripts. The method may further involve repeating steps (a)-(e), where the target sequence in step (a) is supplied by the transcripts. In another aspect, the method in step (b) may include degradation RNA analyte chemically or enzymatically after forming modified probe.

In another aspect, the method includes a kit for detection of a DNA analyte, RNA analyte, such as an RNA viral genome, a siRNA, or a miRNA, having a known target sequence. The kit includes: (a) a single-stranded target probe with hairpin loop structure having a sequence capable of hybridizing with the target sequence, under conditions effective to form a double-stranded heteroduplex complex of the analyte and probe, (b) a polymerase, (c) one to three of the four possible nucleotide triphosphates, (d) a single-stranded DNA detection probe having a sticky end sequence that is complementary to a sticky end sequence of the modified probe, where the detection probe (i) does not hybridize to the target and (ii) contains a promoter region, (e) a polymerase, and (f) a probe, such as a molecular beacon probe, capable of hybridizing to an analyte target sequence, to produce a detectable signal thereby.

In operation of the kit, addition of a target analyte and aqueous medium to a reaction vessel, and addition of the kit components to initiate reactions to (a) form a double-stranded complex of the analyte and target probe, (b) add a selected one or more target-directed nucleotide bases to the target probe's 3' end to produce a modified probe, (c) ligate the modified probe and a detection probe to form a two-probe ligation product, (d) form ligation-product transcripts containing analyte-target sequences, and (e) bind the molecular beacon probes to the transcripts, to produce a detectable signal in the vessel.

For use in detecting a plurality of target sequences of interest in one or more RNA or DNA analytes, the single-stranded DNA target probe may include a plurality of target probes, each having a single-stranded polynucleotides with a hairpin loop structure capable of forming a double-stranded complex with a region of a sample polynucleotide.

The promoter region of the detection probe may be a RNA polymerase promoter, and the promoter-dependent polymerase may be a RNA polymerase. Where the detection probes includes a hairpin structure, the hairpin region itself may function as the promoter region.

These and other objects and features of the invention will be more fully appreciated when the following detailed description of the invention is read in conjunction with the accompanying drawing and the appended claims.

BRIEF DESCRIPTION OF THE FIGURES

FIGS. 2A-2G illustrate steps in practicing the invention in various embodiments;

FIG. 12, upper panel, shows the results of detecting SNP1 and SNP2 with dXTP, and FIG. 12, lower panel, shows the results of detecting SNP3 and SNP4 with dXTP. The specifically detected bands (in lane 1 and 7) are the circularized probes which 3' end of the target probe based-extended, and ligased with detection probe which has a 3' end complementary sequence. 1, 7. dGTP; 2, 8. dCTP; 3, 9. dTTP; 4, 10. dATP; 5, 11. no dXTP; 6, 12. no target;

FIG. 14, upper panel, detection reactions from four synthetic target templates; FIG. 14, middle panel, detection reactions from soybean line PI genomic DNA; FIG. 14, lower panel, detection reactions from soybean line Essex. 1, 2, 3 detect SNP1; 4, 5, 6 detect SNP2; 7, 8, 9 detect SNP3; 10, 11, 12 detect SNP4; 1, 4, 7, 10, single ligation product with potion complementary to antisense primer; 2, 5, 8, 11, multiplex extension-ligation-Exonuclease digested products; 3, 6, 9, 12, mixture of 3 extension-ligation-Exonuclease digested products excluded the ligation product with potion complementary to antisense primer;

DETAILED DESCRIPTION OF THE INVENTION

Figures 1A, 1B:
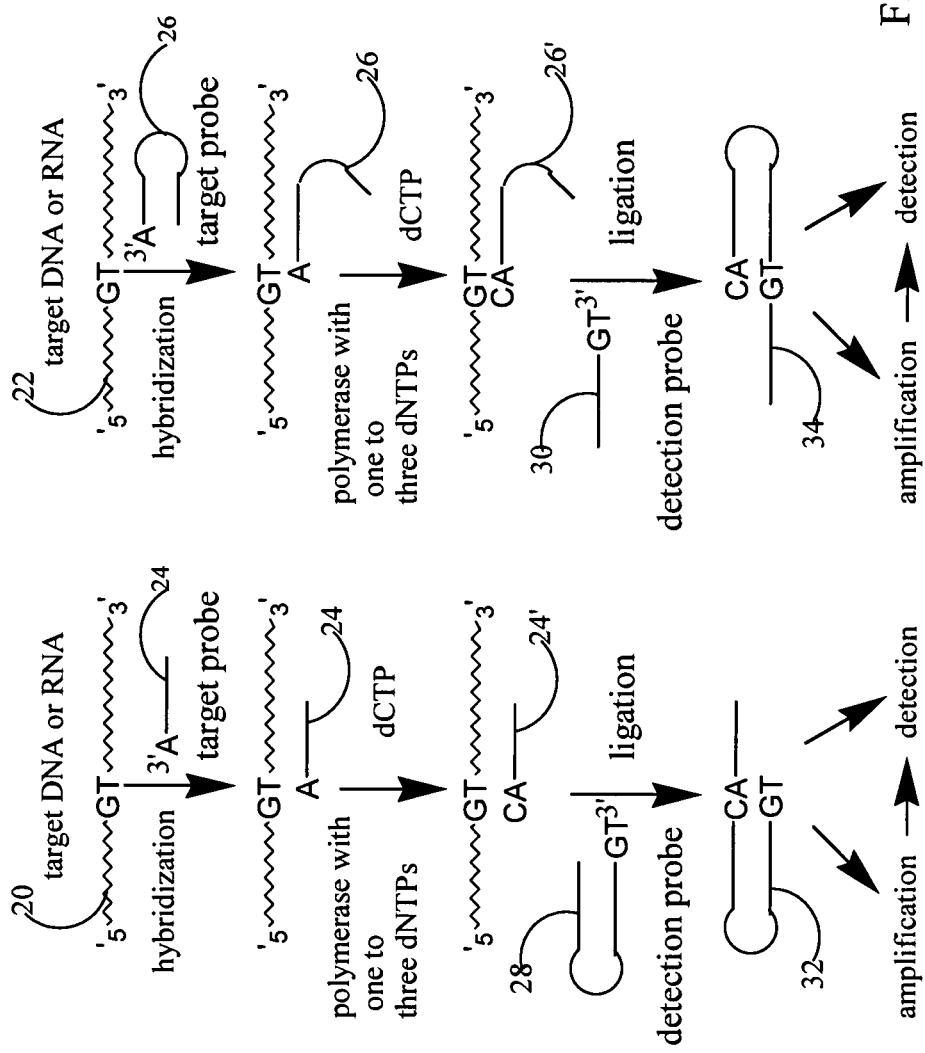
FIGS. 1A and 1B show steps in practicing the method of the invention in one general embodiment that employs a single-stranded target probe and a single-stranded, hairpin detection probe (1A), and a second general embodiment that employs a single-stranded hairpin target probe and a single-stranded detection probe (1B)

The disclosed composition and method make use of certain materials and procedures which allow consistent and quantitative amplification and detection of target nucleic acid sequences. These materials and procedures are described in detail below.

Some major features of the disclosed method are:
1. The hairpin probe is selected to improve hybridization specificity and increase multiplicity.
2. The polymerase operation can be manipulated to generate controlled extension product to obtain allelic discrimination by adding selected one to three of the four nucleotide triphosphate.
3. The ligation operation is template-independent to obtain further allelic discrimination.
4. The template-independent ligation operation provides more flexibility to add desired features to the ligation products, for instance, may contain arbitrarily chosen tag sequences that are useful for amplification and detection.
5. The ligated products may be circular polynucleotides with dumbbell structure, the dumbbell circular DNA has many unique applications.
6. The amplification operation can be manipulated to be isothermal.
7. Signals can be strictly quantitative because in certain embodiments of the amplification operation amplification is linear.
8. Modified nucleotides or other moieties may be incorporated during DNA replication or transcription.

A. DEFINITIONS

The terms below are given the following definitions unless indicated otherwise:

1. "Targeting sequence or target polynucleotides" refers to that portion or region of a polynucleotide probe that is designed to be substantially complementary to a sequence found in an analyte. The "targeting sequence" is also synonomously referred to as the "analyte-specific region" of the probe. Conversely, the sequence in the analyte is referred to as the "targeted sequence". "Target polynucleotide or target sequence" refers to a polynucleotide sequence that is sought to be detected. The target polynucleotide can be obtained from any source, and can comprise any number of different compositional components. For example, the target can be nucleic acid (e.g. DNA or RNA), transfer RNA, siRNA, miRNA, and can comprise nucleic acid analogs or other nucleic acid mimic. The target can be methylated, non-methylated, or both. The target can be bisulfite-treated and non-methylated cytosines converted to uracil. Further, it will be appreciated that "target polynucleotide" can refer to the target polynucleotide itself, as well as surrogates thereof, for example amplification products, and native sequences. In one embodiment, the target polynucleotide is a miRNA molecule. In one embodiment, the target polynucleotide lacks a poly-A tail. In one embodiment, the target polynucleotide is a short DNA molecule derived from a degraded source, such as can be found in for example but not limited to forensics samples (see for example Butler, 2001, Forensic DNA Typing: Biology and Technology Behind STR Markers. The target polynucleotides of the present teachings can be derived from any of a number of sources, including without limitation, viruses, prokaryotes, eukaryotes, for example but not limited to plants, fungi, and animals. These sources may include, but are not limited to, whole blood, a tissue biopsy, lymph, bone marrow, amniotic fluid, hair, skin, semen, biowarfare agents, anal secretions, vaginal secretions, perspiration, saliva, buccal swabs, various environmental samples (for example, agricultural, water, and soil), research samples generally, purified samples generally, cultured cells, and lysed cells. It will be appreciated that target polynucleotides can be isolated from samples using any of a variety of procedures known in the art, for example the Applied Biosystems ABI Prism™ 6100 Nucleic Acid PrepStation, and the ABI Prism™ 6700 Automated Nucleic Acid Workstation, Boom et al., U.S. Pat. No. 5,234,809., mirVana RNA isolation kit (Ambion), etc. It will be appreciated that target polynucleotides can be cut or sheared prior to analysis, including the use of such procedures as mechanical force, sonication, restriction endonuclease cleavage, or any method known in the art. In general, the target polynucleotides of the present teachings will be single stranded, though in some embodiments the target polynucleotide can be double stranded, and a single strand can result from denaturation.

2. A "target probe" is a linear single-stranded nucleic acid molecule or a double stranded nucleic acid molecules including target recognition segment. The recognition segment comprises a polynucleotide probe that recognises the chosen target polynucleotides. The target probe can undergo hybridisation with a complementary sequence of bases in the polynucleotide target to be detected. The sequence of the probe polynucleotide should be at least six bases, preferably between six to fifty and optimally between twelve and thirty, in order to impart specificity to the probe and to ensure secure binding between it and its target. However, such a base sequence need not be a single continuous complementary polynucleotide sequence but can be comprised of two or more individual complementary sequences interrupted by non-complementary sequences.

Useful target probe comprise oligonucleotides, oligonucleotide analogs, or a combination. Target probe can comprise a target recognition portion and, optionally, a non-target recognition portion. The target recognition portion is complementary to sequence in a target template referred to as the probe complement region of the target template. Target probe can contain additional sequence (and/or other features) that is not complementary to any part of the target template. This sequence is referred to as the non-target complement portion of the target probe. The non-target complement portion of the probe, if present, can facilitate, for example, detection, immobilization, or separation of the probe. The non-target complement portion of an target probe may be any length, but is generally 1 to 100 nucleotides long, and preferably 4 to 8 nucleotides long. The non-target complement portion is generally at the 5' end of the probe. To aid in detection and quantitation of extended target probe, target probe can include one or more detection labels. Target probe can, but need not, include non-target complement portion and/or features other than the target complement portion. Thus, for example, target probe may consist of a target complement portion, target probe may comprise a target complement portion, and target probe may comprise nucleotides where the nucleotides consist of a target complement portion.

If the target polynucleotides is double stranded, the target probe can comprise a sense target recognition portion, and a non-target recognition portion may comprise an antisense target complementary portion.

The target probe may be single stranded polynucleotides with or without hairpin structure or double stranded polynucleotides. Both linear single-stranded target probe and double-stranded target probe include target complementary portion and arbitrary sequences portion. For double-stranded target probe, one end of the double stranded target probe is connected through covalent bond. The covalent bond may not use nucleotides as bridge. The other end of double stranded target probe may be a sticky end before or after adding nucleotide triphosphate in step (b). The single strand region of a sticky end may include one or more than one nucleotides.

The linear single-stranded target probe may include predetermined hairpin structure containing short stretches of complementary sequences, perhaps as few as 5 or 6 nucleotides, such that these complementary stretches will anneal to provide a hairpin oligonucleotide. As used herein, the term "hairpin oligonucleotide" refers to a single stranded polynucleotide containing complementary sequences at or near each of its 5'- and 3'-ends such that said complementary sequences anneal, resulting in the formation of a circular structure held in the circularized form by the hydrogen bonded internally complementary sequences. The difference between hairpin oligonucleotides and actual single-stranded DNA circles, such as those formed by the methods disclosed herein, is that the single-stranded circles are held together by covalent bonds to form single circles without free 5'- and 3'-ends. In addition, the starting hairpin oligonucleotides disclosed herein contain internal complementary sequences that are inverted relative to each other so that the 3'- and 5'-ends, where said sequences are located, will hybridize within the same segment to yield a short linear segment with only the non-hybridized portion of the polynucleotide forming a circular structure. In addition, there may be only one of said complementary sequences will be located at either the 5'- or 3'-end of the polynucleotide with the other complementary sequence being displaced from the end of said polynucleotide by a short segment of nucleotides that is not complementary to any portion of the polynucleotide of which it is a part.

The arbitrary sequence portions included in linear single-stranded target probe and double-stranded target probe are determined by desires, inclinations and motivations of the user of the present invention. For instance, the arbitrary sequence may include promoter site, restriction enzyme site, universal primer site, cleavage site, the address tag portion, detection tag portion, unnatural nucleotides, etc.

Target probes can be made in a variety of ways. They may be synthesized chemically, e.g., according to the solid phase phosphoramidite triester method described by Beaucage and Caruthers (1981), Tetrahedron Letts., 22(20):1859-1862, e.g., using an automated synthesizer, as described in Needham-VanDevanter et al. (1984) Nucleic Acids Res., 12:6159-6168. Oligonucleotides can also be custom made and ordered from a variety of commercial sources known to persons of skill. Purification of oligonucleotides, where necessary, is typically performed by either native acrylamide gel electrophoresis or by anion-exchange HPLC as described in Pearson and Regnier (1983) J. Chrom. 255:137-149. The sequence of the synthetic oligonucleotides can be verified using the chemical degradation method of Maxam and Gilbert (1980) in Grossman and Moldave (eds.) Academic Press, NY, Methods in Enzymology 65:499-560. Custom oligos can also easily be ordered from a variety of commercial sources known to persons of skill.

In one embodiment, a mixture of plurality of target probes may be synthesized from a flat solid surface. Releasing the plurality of target probe from solid surface forms a mixture of plurality of target probes. The mixture of plurality of target probes may be used for detecting a plurality of target sequences of interest in one or more polynucleotides in a sample.

Where target probes are prepared by synthetic methods, it may be necessary to phosphorylate the 5' end of the probe, since oligonucleotide synthesizers do not usually produce oligonucleotides having a phosphate at their 5' end. The absence of a phosphate at the 5' end of the probe would otherwise prevent ligation of the 5' and 3' ends of the probe. Phosphorylation may be carried out according to methods well known in the art, e.g., using T4 polynucleotide kinase as described, e.g., in U.S. Pat. No. 5,593,840.

3. A "modified probe" as used herein refers to a target probe that has been changed in structure, sequence and/or composition as the result of a reaction that is dependent upon the probe having hybridized to a particular polynucleotide sequence ("targeted sequence") in an analyte. In one embodiment of current invention, the modified probe is the target probe that has been extended by limited bases due to selected added one to three of four nucleotide triphosphates.

The current invention is different from traditional single base extension (SBE; sometimes referred to as "minisequencing"). Single base extension or minisequencing methods use at least one of labeled or modified dNTPs for allelic discrimination. Generally, the nucleotide is derivatized such that no further extensions can occur, so only a single nucleotide is added. The following references, relating to SBE, are hereby expressly incorporated by reference in their entirety: U.S. Pat. No. 5,639,611; U.S. Pat. No. 5,824,476; U.S. Pat. No. 5,981, 176; U.S. Pat. No. 4,851,331; U.S. Pat. No. 5,888,819; U.S. Pat. No. 6,004,744; U.S. Pat. No. 5,137,806; U.S. Pat. No. 6,287,778 B1; U.S. Pat. No. 5,582,970; U.S. Pat. No. 6,307, 039; U.S. Pat. No. 6,013,431; U.S. Pat. No. 5,846,710; U.S. Pat. No. 5,710,028; U.S. Pat. No. 6,153,379; U.S. Pat. No. 5,665,539; U.S. Pat. No. 6,287,778; U.S. Pat. No. 5,856,092; WO 92/15712; U.S. Pat. No. 4,656,127; EPO 371437 B1; U.S. Pat. No. 5,595,890; U.S. Pat. No. 6,015,675; U.S. Pat. No. 5,578,458. The present invention does not rely on modified dNTPs, but uses subsequent ligation reaction for allelic discrimination. Only correctly extended target probes will be able to be ligated with detection probes to be detected.

4. A "detection probe" is a linear single-stranded nucleic acid molecule or a double stranded nucleic acid molecules including complementary portion to hybridize to modified target probe in step (b). The complementary portion locates from either 3' end or 5' end and is a linear single stranded. The modified target probe can undergo hybridisation with a complementary portion of bases in the detection probe to be detected. The sequence of complementary portion should be at least one base, preferably between two to fifteen and optimally between two to three bases.

The 3' end or 5' end of detection probe does not hybridize to sense target sequences that target probe hybridize to, but may be partially complementary with anti-sense target sequences.

Useful detection probe comprise oligonucleotides, oligonucleotide analogs, or a combination. Detection probe can contain additional sequence (and/or other features) that is not complementary to any part of the modified target probe. This sequence is referred to as the non-target probe complement portion of the detection probe. The non-target probe complement portion of the probe, if present, can facilitate, for example, detection, immobilization, or separation of the probe. The non-target probe complement portion of a detection probe may be any length, but is generally 1 to 100 nucleotides long, and preferably 4 to 8 nucleotides long. The non-target probe complement portion is generally at either 5' end or 3' end of the probe. To aid in detection and quantitation of modified target probe, detection probe can include one or more detection labels. For instance, the non target probe complementary portion may include promoter site, restriction enzyme site, primer site, cleavage site, the address tag portion, detection tag portion, unnatural nucleotides, etc.

The detection probe may be single stranded polynucleotides with hairpin structure or double stranded polynucleotides. Both linear single-stranded detection probe and double-stranded detection probe include target probe complementary portion and arbitrary sequences portion. For double-stranded detection probe, one end of the double stranded target probe may or may not be connected through covalent bond. The covalent bond may not use nucleotides as bridge. The other end of double stranded target probe may be a sticky end. The single strand region from the end of a sticky end may include one or more than one nucleotides.

The linear single-stranded detection probe may include predetermined hairpin structure similar to target probe, except that there is not any portion to hybridize to target sequences.

Where detection probes are prepared by synthetic methods, it may be necessary to phosphorylate the 5' end of the probe, since oligonucleotide synthesizers do not usually produce oligonucleotides having a phosphate at their 5' end. The absence of a phosphate at the 5' end of the probe would otherwise prevent ligation of the 5' and 3' ends of the probe. Phosphorylation may be carried out according to methods well known in the art, e.g., using T4 polynucleotide kinase as described, e.g., in U.S. Pat. No. 5,593,840.

5. "Ligation products" are produced from ligation detection probes with modified probes. The ligation products may be a linear single-stranded polynucleotides with hairpin structure or a double stranded polynucleotides or linear circular polynucleotides.

In the case of linear circular ligation products produced, unreacted probes can contribute to backgrounds from undesired non-specific amplification. In a preferred embodiment, any unreacted precircle probes and/or target sequences are rendered unavailable for amplification. This can be done in a variety of ways, as will be appreciated by those in the art. In one embodiment, exonucleases are added, that will degrade any linear nucleic acids, leaving the closed circular products. Suitable 3'-exonucleases include, but are not limited to, exo I, exo III, exo VII, exo V, and polymerases, as many polymerases have excellent exonuclease activity, etc. Prior to amplification, any exonuclease must be eliminated from the reaction mixture, e.g., by heat denaturation of the nuclease.

There are many other desired methods by those in the art can be included and used to enrich ligation products (U.S. Pat. No. 6,858,412, U.S. Pat. No. 6,329,150).

A ligation product may include many unique features inherited from detection probe or target probe for detection and amplification purposes. For instance, a ligation product may include at least one promoter site, restriction enzyme site, primer site, cleavage site, the address tag portion, detection tag portion, unnatural nucleotides, etc.

A "universal" priming site is a site to which a universal primer will hybridize. In general, "universal" refers to the use of a single primer or set of primers for a plurality of amplification reactions. For example, in the detection or genotyping of a multiple different target sequences, all the target probes may share the identical universal priming sequences, allowing for the multiplex amplification of the multiple different ligation products using a single set of primers. This allows for ease of synthesis (e.g. only one set of primers is made), resulting in reduced costs, as well as advantages in the kinetics of hybridization. Most importantly, the use of such primers greatly simplifies multiplexing to amplify a plurality of ligation products. It should also be noted that "sets" of universal priming sequences/primers may be used. For example, in highly multiplexed reactions, it may be useful to use several sets of universal sequences, rather than a single set; for example, one group of different ligation products may have the same priming sequences, and the other group of different ligation products has a different set, etc.

A cleavage site is a site that allows cleavage of nucleic acids in specific locations. Suitable cleavage sites include, but are not limited to, the incorporation of uracil or other ribose nucleotides, restriction endonuclease sites, etc. In a preferred embodiment, the cleavage site comprises a uracil base. This allows the use of uracil-N-glycolylase, an enzyme which removes the uracil base while leaving the ribose intact. This treatment, combined with changing the pH (to alkaline) by heating, or contacting the site with an apurinic endonuclease that cleaves basic nucleosides, allows a highly specific cleavage of the ligated products. There might be more than one cleavage sites included.

Address tag portions are added to ligation products or amplicons of ligation products to allow separation of nucleic acid fragment pools. One preferred form of address tag portions are hybridization tag sequences. In this embodiment address tag portions are chosen so as to allow hybridization to the complementary capture probes on a surface or solid support of an array. Address tag portions serve as unique identifiers of the ligation products. In general, sets of address tags and the corresponding capture probes are developed to minimize cross-hybridization with both each other and other components of the reaction mixtures, including the target sequences and sequences on the larger nucleic acid sequences outside of the target sequences (e.g. to sequences within genomic DNA). Other forms of address tags are mass tags that can be separated using mass spectroscopy, electrophoretic tags that can be separated based on electrophoretic mobility, or column chromatography, etc.

Address tags for detection in array hybridization, e.g., high density arrays, are preferably around 20 nucleotides long and are described, e.g., in Shoemaker et al. (1996) Nature Genetics 14: 450. Address tag sequences should be maximally different yet still retain similar hybridization properties to facilitate simultaneous analysis on high-density oligonucleotide arrays. As described in Shoemaker et al., supra, an algorithm can be used to select sets of thousands (over 9,000) maximally distinguished 20mer address tag sequences that are predicted to have similar melting temperatures, no secondary structures and no extensive similarity between any two sequences (more than 5 mismatches). Moreover, hybridizations are sensitive and capable of detecting small differences in hybridization signal. For example, as further described in Shoemaker et al., supra, a two fold change in concentration was detected in the presence of a hybridization mixture with 120 oligonucleotides.

The use of address tags allow the use of "universal arrays", e.g. arrays can be made with one set of capture probes that can be used in a wide variety of applications. The use of address tag sequences that allow the use of universal arrays has been described in limited contexts; see for example Chee et al., Nucl. Acid Res. 19:3301 (1991); Shoemaker et al., Nature Genetics 14:450 (1998); Barany, F. (1991) Proc. Natl. Acad. Sci. USA 88:189-193; EP 0 799 897 A1; WO 97/31256, all of which are expressly incorporated by reference.

In one embodiment, address tags are used but not their hybridization properties. Rather, different length address tags can be used, alternatively, the sequence the address tag is altered to result in different molecular weights. What is important is this embodiment is that each address tag has a different molecular weight. The address tags are cleaved from the rest of the amplicon as described herein and subjected to mass spectroscopy analysis, or other techniques that rely on differential molecular weights for separation, such as gel electrophoresis.

6. The term "amplification" refers to amplification, duplication, multiplication, or multiple expression of ligation product, in vivo or in vitro, yielding about 2.5 fold or more copies. The 2.5 fold figure is due to current detection limit, rather than a biological state. If the ligation products are circular polynucleotides. The circular ligation products may be cleaved before amplification. As will be appreciated by those in the art, there are a wide variety of suitable amplification techniques that can be used to amplify ligation products or cleaved ligation products to form the amplicons of the invention that are then detected, generally via the use of arrays, as is more fully outlined below. Suitable amplification methods include both target amplification and signal amplification and include, but are not limited to, polymerase chain reaction (PCR), ligation chain reaction (sometimes referred to as oligonucleotide ligase amplification OLA), cycling probe technology (CPT), strand displacement assay (SDA), Rolling circle amplification (RCA), transcription mediated amplification (TMA), nucleic add sequence based amplification (NASBA), and invasive cleavage technology. All of these methods require a primer nucleic acid (including nucleic acid analogs) that is hybridized to a target sequence to form a hybridization complex, and an enzyme is added that in some way modifies the primer to form a modified primer. For example, PCR generally requires two primers, dNTPs and a DNA polymerase; LCR requires two primers that adjacently hybridize to the target sequence and a ligase; CPT requires one cleavable primer and a cleaving enzyme; invasive cleavage requires two primers and a cleavage enzyme; etc. Thus, in general, a ligation product is added to a reaction mixture that comprises the necessary amplification components, and amplicons are formed. In contrast, transcription to amplify ligation products may not need primers. The amplification can be initiated from promoter sequence included within the ligation products. In another aspect, special structure, such as loop sequences within the ligation products can be used to initiate the transcription.

In general, the amplicon comprises a detectable label, such as a fluorescent label, which is either incorporated by the enzyme or present on the original primer. As required, the unreacted primers are removed, in a variety of ways, as will be appreciated by those in the art. The hybridization complex is then disassociated, and the amplicon is detected and optionally quantitated by an array. In some cases, the first amplicon serves as a target sequence for a secondary reaction, which then produces a number of second amplicons, which can be detected. For instance, the transcripts can be used as target to repeat the amplification process.

Accordingly, the reaction starts with the addition of a primer nucleic acid to the ligation products which forms a hybridization complex. Once the hybridization complex between the primer and the ligated products has been formed, an enzyme, sometimes termed an "amplification enzyme", is used to modify the primer. As for all the methods outlined herein, the enzymes may be added at any point during the assay, either prior to, during, or after the addition of the primers. The identity of the enzyme will depend on the amplification technique used. Similarly, the modification will depend on the amplification technique. In contrast, primer is not needed for transcription amplification. The transcription enzymes will bind with special sequences of ligation products to initiate amplification.

Once the enzyme has modified the primer to form an amplicon, the hybridization complex is disassociated. In one aspect, dissociation is by modification of the assay conditions. In another aspect, the modified primer no longer hybridizes to the ligation products and dissociates. Either one or both of these aspects can be employed in signal and target amplification reactions as described below. Generally, the amplification steps are repeated for a period of time to allow a number of cycles, depending on the number of copies of the original target sequence and the sensitivity of detection, with cycles ranging from 1 to thousands, with from 10 to 100 cycles being preferred and from 15 to 50 cycles being especially preferred. In certain embodiments, e.g., where one desires quantifying a specific sequence, it may be desirable to perform several parallel amplification reactions each using a different number of cycles, such that at least in one set of reactions, the amplification reaction will be in the exponential phase, and will therefore provide a direct correlation between the level of amplified product and the number of original sequences.

In a preferred embodiment, the ligation product or target amplification is PCR (Polymerase Chain Reaction). The ligated products can be amplified by PCR before and after it has been treated enzymatically. For instance, the circular ligated products can be cleaved and then amplified by PCR. "Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al., editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature>90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred µL, e.g. 200 µL. "Reverse transcription PCR," or "RT-PCR," means a PCR that is preceded by a reverse transcription reaction that converts a target RNA to a complementary single stranded DNA, which is then amplified, e.g. Tecott et al., U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al., U.S. Pat. No. 5,210,015 ("taqman"); Wittwer et al., U.S. Pat. Nos. 6,174,670 and 6,569,627 (intercalating dyes); Tyagi et al., U.S. Pat. No. 5,925,517 (molecular beacons); which patents are incorporated herein by reference. Detection chemistries for real-time PCR are reviewed in Mackay et al., Nucleic Acids Research, 30: 1292-1305 (2002), which is also incorporated herein by reference.

In another embodiment, the circular ligation products can be amplified by Rolling Circle Amplification (RCA). Rolling circle amplification is initiated when nucleotide triphosphates and polymerase are combined with a circular oligonucleotide template. RCA technologies can be used in solution, in situ and in microarrays. In solid phase formats, detection and quantitation can be achieved at the level of single molecules (Lizardi et al., 1998). In the case of linear DNA synthesis, a primed circular template is utilized. At least two types of nucleotide triphosphate, along with an effective catalytic amount of the desired polymerase enzyme are used in the reaction. In DNA synthesis, the polymerase starts at the primer, elongates it, and continues around the circle, making the desired oligonucleotide product sequence. It continues past the starting point, displacing the synthesized DNA (or RNA) as it goes, and proceeds many times around the circle. The process is similar for RNA synthesis, except that the polymerase can initiate synthesis at any point on the circular template and without the aid of a primer. This amplified run-on synthesis produces a long single multimer strand which is made up of many end-to-end copies of the nucleotide sequence complementary to the circular template sequence, and contains multiple copies of the desired oligonucleotide product. Very high yields of amplified products can be obtained with exponential (or cascade) rolling circle amplification (U.S. Pat. Nos. 5,854,033 and 6,143,495; PCT Application No. WO 97/19193) and multiply-primed rolling circle amplification (Dean et al., Genome Research 11:1095-1099 (2001)).

In a preferred embodiment, the ligation products can be transcribed by RNA polymerase. Any RNA polymerase which can carry out transcription in vivo or vitro and for which promoter sequences have been identified can be used in or with the disclosed method. Stable RNA polymerases without complex requirements are preferred. Proc. Natl. Acad. Sci. USA 81:2035-2039 (1984)), and SP6 RNA polymerase (Butler and Chamberlin, J. Biol. Chem. 257:5772-5778 (1982)) which are highly specific for particular promoter sequences (Schenborn and Meirendorf, Nucleic Acids Research 13:6223-6236 (1985)). Other RNA polymerases with this characteristic are also preferred. Generally, the RNA polymerase selected is capable of transcribing from the promoter sequence provided by a double strand T7 promoter or a hairpin detection probe with double strand T7 promoter stem as described herein. Numerous promoter sequences are known and any suitable RNA polymerase having an identified promoter sequence can be used.

For circular template, the process for transcription synthesis can be initiated at any point on the circular template and without the aid of a primer or promoter sequence. This amplified run-on synthesis produces a long single multimer strand which is made up of many end-to-end copies of the nucleotide sequence complementary to the circular template sequence, and contains multiple copies of the desired oligonucleotide product.

7. "Detection labels." To aid in detection and quantitation of nucleic acids amplified in present invention, detection labels can be directly incorporated into amplified nucleic acids or can be coupled to detection molecules. As used herein, a detection label is any molecule that can be associated with amplified nucleic acid, directly or indirectly, and which results in a measurable, detectable signal, either directly or indirectly. Many such labels for incorporation into nucleic acids or coupling to nucleic acid or antibody probes are known to those of skill in the art.

In this embodiment, the label(s) may be incorporated in a variety of ways: (1) the primers comprise the label(s), for example attached to the base, a ribose, a phosphate, or to analogous structures in a nucleic acid analog; (2) modified nucleosides are used that are modified at either the base or the ribose (or to analogous structures in a nucleic acid analog) with the label(s); these label-modified nucleosides are then converted to the triphosphate form and are incorporated into a newly synthesized strand by an extension enzyme such as a polymerase; (3) modified nucleotides are used that comprise a functional group that can be used (post-enzymatic reaction) to add a detectable label; (4) modified primers are used that comprise a functional group that can be used to add a detectable label in a similar manner; or (5) a label probe that is directly labeled and hybridizes to a portion of the amplicon can be used. Any of these methods result in a detectable amplicon.

Examples of suitable fluorescent labels include fluorescein, 5,6-carboxymethyl fluorescein, Texas red, nitrobenz-2-oxa-1,3-diazol-4-yl (NBD), coumarin, dansyl chloride, and rhodamine. Preferred fluorescent labels are fluorescein (5-carboxyfluorescein-N-hydroxysuccinimide ester) and rhodamine (5,6-tetramethyl rhodamine). These can be obtained from a variety of commercial sources, including Molecular Probes, Eugene, Oreg. and Research Organics, Cleveland, Ohio.

Labeled nucleotides are preferred form of detection label since they can be directly incorporated into the ligation products or amplified ligation product. Examples of detection labels that can be incorporated into amplified DNA or RNA include nucleotide analogs such as BrdUrd (Hoy and Schimke, Mutation Research 290:217-230 (1993)), BrUTP (Wansick et al., J. Cell Biology 122:283-293 (1993)) and nucleotides modified with biotin (Langer et al., Proc. Natl. Acad. Sci. USA 78:6633 (1981)) or with suitable haptens such as digoxygenin (Kerkhof, Anal. Biochem. 205:359-364 (1992)). Suitable fluorescence-labeled nucleotides are Fluorescein-isothiocyanate-dUTP, Cyanine-3-dUTP and Cyanine-5-dUTP (Yu et al., Nucleic Acids Res., 22:3226-3232 (1994)). A preferred nucleotide analog detection label for DNA is BrdUrd (BUDR triphosphate, Sigma), and a preferred nucleotide analog detection label for RNA is Biotin-16-uridine-5'-triphosphate (Biotin-16-dUTP. Boehringher Mannheim).

Detection labels that are incorporated into amplified nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo[3.3.1.1.sup.3,7]decane]-4-yl)phenyl phosphate; Tropix, Inc.).

A preferred detection label for use in detection of amplified RNA is acridinium-ester-labeled DNA probe (GenProbe, Inc., as described by Arnold et al., Clinical Chemistry 35:1588-1594 (1989)). An acridinium-ester-labeled detection probe permits the detection of amplified RNA without washing because unhybridized probe can be destroyed with alkali (Arnold et al. (1989)).

Molecules that combine two or more of these detection labels are also considered detection labels. Any of the known detection labels can be used with the disclosed probes, tags, and method to label and detect nucleic acid amplified using the disclosed method. Methods for detecting and measuring signals generated by detection labels are also known to those of skill in the art. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. Such methods can be used directly in the disclosed method of amplification and detection. As used herein detection molecules are molecules which interact with amplified nucleic acid and to which one or more detection labels are coupled.

In one embodiment, the label is a mass tag by detecting the molecular weights of the amplification product or a fragment thereof, such as by chromatography or mass spectroscopy.

In another embodiment, detection in the present invention by the terms length determination, separation-by-length assay, and separation-by-length assay medium are taken collectively to mean a process and its related apparatus that achieves separation of DNA fragments on the basis of length, size, mass, or any other physical property. This includes generally, liquid chromatography, electrophoresis and direct mass spectrometry; more particularly, high performance liquid chromatography (HPLC) and capillary electrophoresis or gel electrophoresis, and MALDI-TOF MS respectively.

8. "Microarray or Array." One preferred aspect of the present invention is that it results in high-throughput screening capabilities. In the assays described herein, from a few up to millions of different address tags or detection tags resulted from amplified ligation products identifying, e.g., SNPs, can be identified simultaneously by using microarray. For example, using simple dot-blot hybridization methods, membranes with thousands of immobilized probes can be generated for screening against tags resulted from amplification pool of ligated products. The solid-phase techniques described below can be adapted to having literally millions of different immobilized nucleic acids per square inch. Similarly, very large sets of amplified DNAs, e.g., tags, can be immobilized on membranes for simultaneous screening against one or more sequences generated from ligation products.

"Microarray" or "array" refers to a solid phase support having a planar surface, which carries an array of nucleic acids, each member of the array comprising identical copies of an oligonucleotide or polynucleotide immobilized to a spatially defined region or site, which does not overlap with those of other members of the array; that is, the regions or sites are spatially discrete. Spatially defined hybridization sites may additionally be "addressable" in that its location and the identity of its immobilized oligonucleotide are known or predetermined, for example, prior to its use. Ordered arrays include, but are not limited to, those prepared by photolithography, spotting, printing, electrode arrays, "gel pad" arrays, and the like. The size of array can vary from one element to thousands, tens of thousands, or even millions of elements. Depending on the number of array elements required, some array types or methods of preparing the array may be more advantageous, as those skilled in the art are aware. Typically, the oligonucleotides or polynucleotides are single stranded and are covalently attached to the solid phase support, usually by a 5'-end or a 3'-end. The density of non-overlapping regions containing nucleic acids in a microarray is typically greater than 100 per $cm^2$, and more preferably, greater than 1000 per $cm^2$. Microarray technology is reviewed in the following references: Schena, Editor, Microarrays: A Practical Approach (IRL Press, Oxford, 2000); Southern, Current Opin. Chem. Biol., 2: 404-410 (1998); Nature Genetics Supplement, 21: 1-60 (1999). As used herein "microarray" or "array" may also refer to a "random microarray" or "random array", which refer to an array whose spatially discrete regions of oligonucleotides or polynucleotides are not spatially addressed. That is, the identity of the attached oligonucleoties or polynucleotides is not discernable, at least initially, from its location. In one aspect, random microarrays are planar arrays of microbeads wherein each microbead has attached a single kind of hybridization tag complement, such as from a minimally cross-hybridizing set of oligonucleotides. Arrays of microbeads may be formed in a variety of ways, e.g. Brenner et al., Nature Biotechnology, 18: 630-634 (2000); Tulley et al., U.S. Pat. No. 6,133,043; Stuelpnagel et al., U.S. Pat. No. 6,396,995; Chee et al., U.S. Pat. No. 6,544,732; and the like. Likewise, after formation, microbeads, or oligonucleotides thereof, in a random array may be identified in a variety of ways, including by optical labels, e.g. fluorescent dye ratios or quantum dots, shape, sequence analysis, or the like.

The construction and use of solid phase nucleic acid arrays to detect target nucleic acids is well described in the literature. See, Fodor et al. (1991) Science, 251: 767-777; Sheldon et al. (1993) Clinical Chemistry 39(4): 718-719; Kozal et al. (1996) Nature Medicine 2(7): 753-759 and Hubbell U.S. Pat. No. 5,571,639. See also, Pinkel et al. PCT/US95/16155 (WO 96/17958). In brief, a combinatorial strategy allows for the synthesis of arrays containing a large number of probes using a minimal number of synthetic steps. For instance, it is possible to synthesize and attach all possible DNA 8 mer oligonucleotides (48, or 65,536 possible combinations) using only 32 chemical synthetic steps. In general, VLSIPS TM procedures provide a method of producing 4n different oligonucleotide probes on an array using only 4n synthetic steps. Methods of adding, washing and detecting the amplification products on the array are well known.

9. "Complementary or substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference. The various hybridization regions, or tags, and primers herein are selected to be "substantially" complementary to their intended hybridization partner. This means that the regions or primers must be sufficiently complementary to hybridize with their respective strands under the given hybridization or polymerization conditions. Therefore, the polynucleotide sequence need not reflect the exact sequence of the complement. For example, a non-complementary nucleotide sequence may be attached to the 5' end of the primer, with the remainder of the primer sequence being complementary to the strand. Alternatively, non-complementary bases or longer sequences can be interspersed into the region or the primer, provided that the polynucleotide sequence has sufficient complementarity with the sequence of the strand to be hybridized therewith and thereby form a duplex of sufficient stability or structure for the subsequent operation to be performed.

10. "Hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1M, more usually less than about 500 mM and less than about 200 mM. Hybridization temperatures can be as low as 5° C., but are typically greater than 22° C., more typically greater than about 30° C., and preferably in excess of about 37° C. Hybridizations are usually performed under stringent conditions, i.e. conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at s defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see for example, Sambrook, Fritsche and Maniatis. "Molecular Cloning A laboratory Manual" $2^{nd}$ Ed. Cold Spring Harbor Press (1989) and Anderson "Nucleic Acid Hybridization" $1^{st}$ Ed., BIOS Scientific Publishers Limited (1999), which are hereby incorporated by reference in its entirety for all purposes above. "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

11. "Hybridization-based assay" means any assay that relies on the formation of a stable duplex or triplex between a probe and a target nucleotide sequence for detecting or measuring such a sequence. In one aspect, probes of such assays anneal to (or form duplexes with) regions of target sequences in the range of from 8 to 100 nucleotides; or in other aspects, they anneal to target sequences in the range of from 8 to 40 nucleotides, or more usually, in the range of from 8 to 20 nucleotides. A "probe" in reference to a hybridization-based assay mean a polynucleotide that has a sequence that is capable of forming a stable hybrid (or triplex) with its complement in a target nucleic acid and that is capable of being detected, either directly or indirectly. Hybridization-based assays include, without limitation, assays based on use of oligonucleotides, such as polymerase chain reactions, NASBA reactions, oligonucleotide ligation reactions, single-base extensions of primers, circularizable probe reactions, allele-specific oligonucleotides hybridizations, either in solution phase or bound to solid phase supports, such as microarrays or microbeads. There is extensive guidance in the literature on hybridization-based assays, e.g. Hames et al., editors, Nucleic Acid Hybridization a Practical Approach (IRL Press, Oxford, 1985); Tijssen, Hybridization with Nucleic Acid Probes, Parts I & II (Elsevier Publishing Company, 1993); Hardiman, Microarray Methods and Applications (DNA Press, 2003); Schena, editor, DNA Microarrays a Practical Approach (IRL Press, Oxford, 1999); and the like. In one aspect, hybridization-based assays are solution phase assays; that is, both probes and target sequences hybridize under conditions that are substantially free of surface effects or influences on reaction rate. A solution phase assay may include circumstance where either probes or target sequences are attached to microbeads.

12. "Kit" refers to any delivery system for delivering materials or reagents for carrying out a method of the invention. In the context of assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials for assays of the invention. In one aspect, kits of the invention comprise probes specific for interfering polymorphic loci. In another aspect, kits comprise nucleic acid standards for validating the performance of probes specific for interfering polymorphic loci. Such contents may be delivered to the intended recipient together or separately. For example, a first container may contain an enzyme for use in an assay, while a second container contains probes.

13. "Polymerase" refers to a catalyst, usually an enzyme, for forming an extension of an oligonucleotide along a DNA or RNA template where the extension is complementary to the template. The nucleotide polymerase is a template dependent polynucleotide polymerase and utilizes nucleoside triphosphates as building blocks for extending the 3'-end of a oligonucleotide to provide a sequence complementary with the single stranded portion of the polynucleotide to which the oligonucleotide is hybridized to form a duplex.

Usually, the catalysts are enzymes, and can be either RNA polymerase, DNA polymerases or reverse transcriptases depending on the template. Such enzymes may be derived from any source such as cells, bacteria, such as E. coli, plants, animals, virus, thermophilic bacteria, and so forth wherein the polymerase may be modified chemically or through genetic engineering to provide for thermal stability and/or increased activity. Such enzymes include Pfu DNA polymerase (native and recombinant) from Stratagene, La Jolla, Calif., Ultma DNA polymerase from Perkin Elmer, Foster City, Calif., rBst DNA polymerase from Epicentre Technologies, Madison, Wis., VENT DNA polymerase from New England Biolabs, Beverly, Mass., Tli DNA polymerase from Promega Corp., Madison, Wis., and Pwo DNA polymerase from Boehringer Mannheim, Indianapolis, Ind., and the like. Amplitaq Stoffel fragment (Applied Biosystems, Foster City, Calif.), or T7 DNA polymerase (Amersham) or Klenow fragment of DNA polymerase I (New England Biolabs)), AMV RNA polymerase NEB), MMLV RNA polymerase (Invitrogen), Powerscript RNA polymerase (Clontech), Superscript RNA polymerase (Invitrogen), etc. but are not limited to these. The polymerase used in the present method are usually thermally stable nucleotide polymerases (e.g., Amplitaq Stoffel fragment) so as to further repeat the denature-annealing and base-extension procedures to increase the number of base-added target probes. Preferably, the polymerase does not possess substantial nicking activity. Preferably, the polymerase which lack 3'→5' exonuclease activity so as to minimize degradation of probe. Mutant polymerases in which the 3'→5' exonuclease activity has been deleted, are known in the art and are suitable for the base-adding methods described herein.

Reverse transcriptases useful in the disclosed method can be any polymerase that exhibits reverse transcriptase activity. The catalytic activities useful in the disclosed method are an RNA-dependent DNA polymerase activity. The reverse transcriptase can have a RNAse H activity or can lack an RNAse H activity. It is preferred that a reverse transcriptase having an RNAse H activity be used add bases to the 3'-end of the target probe. The RNA target can then be digested by RNAse H or a reverse transcriptase having an RNAse H activity, including those derived from Moloney murine leukemia virus (MMLV-RT), avian myeloblastosis virus (AMV-RT). Many other reverse transcriptases, for example, Superscript II or III reverse transcriptase which lacks RNAse H activity and which has RNA-dependent DNA polymerase activity, can be used with addition source of RNAse H, Powerscript (clontech), Arrayscript (Ambion).

14. "Sticky end" refers to an end of DNA in which one strand of the double helix extends a few units beyond the other.

15. "Ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whitely et al., U.S. Pat. No. 4,883,750; Letsinger et al., U.S. Pat. No. 5,476,930; Fung et al., U.S. Pat. No. 5,593,826; Kool, U.S. Pat. No. 5,426,180; Landegren et al., U.S. Pat. No. 5,871,921; Xu and Kool, Nucleic Acids Research, 27: 875-881 (1999); Higgins et al., Methods in Enzymology, 68: 50-71 (1979); Engler et al., The Enzymes, 15: 3-29 (1982); and Namsaraev, U.S. Patent Publication No. 2004/0110213. Many suitable ligases are known, such as T4 DNA ligase (Davis et al., Advanced Bacterial Genetics—A Manual for Genetic Engineering (Cold Spring Harbor Laboratory, Cold Spring Harbor, N.Y., 1980)), E. coli DNA ligase (Panasnko et al., J. Biol. Chem. 253:4590-4592 (1978)), AMPLIGASE® (Kalin et al., Mutat. Res., 283(2):119-123 (1992); Winn-Deen et al., Mol Cell Probes (England) 7(3):179-186 (1993)), Taq DNA ligase (Barany, Proc. Natl. Acad. Sci. USA 88:189-193 (1991), *Thermus thermophilus* DNA ligase (Abbott Laboratories), *Thermus scotoductus* DNA ligase and *Rhodothermus marinus* DNA ligase (Thorbjarnardottir et al., Gene 151:177-180 (1995)). T4 DNA ligase is preferred for ligations involving RNA target sequences due to its ability to ligate DNA ends involved in DNA:RNA hybrids (Hsuih et al., Quantitative detection of HCV RNA using novel ligation-dependent polymerase chain reaction, American Association for the Study of Liver Diseases (Chicago, III., Nov. 3-7, 1995)).

A popular template driven ligation assay for nucleic acid amplification and detection is oligonucleotide ligation assay (OLA), sometimes referred to as the ligation chain reaction (LCR). The method can be run in two different ways; in a first embodiment, only one strand of a target sequence is used as a template for ligation (OLA); alternatively, both strands may be used (OLA). Oligonucleotide ligation amplification ("OLA", sometimes referred to herein as the ligation chain reaction (LCR)) involves the ligation of two smaller probes into a single long probe, using the target sequence as the template. See generally U.S. Pat. Nos. 5,185,243 5,679,524 and 5,573,907; EP 0 320 308 B1; EP 0 336 731 B1; EP 0 439 182 B1; WO 90/01069; WO 89/12696; and WO 97/31256, WO 89/09835, and U.S. Ser. Nos. 60/078,102 and 60/073,011, all of which are incorporated by reference.

One unique feature of current invention is template independent ligation assay for nucleic acid amplification and detection. The ligation between detection probe and modified target probe is not directed by template, but by sticky ends to brought the two probes adjacent to be ligated. Detection probe does not hybridize to target polynucleotides. Only correct extended target probe will be able to hybridize with detection probe to be ligated to form ligated products.

16. "Nucleotide" as used herein includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al., Exp. Opin. Ther. Patents, 6: 855-870 (1996); Mesmaeker et al., Current Opinion in Structual Biology, 5: 343-355 (1995); and the like. Exemplary types of polynucleotides that are capable of enhancing duplex stability include oligonucleotide N3'→P5' phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids (LNAs), and like compounds. Such oligonucleotides are either available commercially or may be synthesized using methods described in the literature.

17. "Polymorphism or genetic variant." The present invention can be used for detection of polymorphism or genetic variations including variations in one or more consecutive or non-consecutive nucleotides in a nucleic acid sample. Exemplary variable regions include SNPs. Certain SNPs have two alleles, others have three alleles and yet others have four alleles. The presence of SNPs may be indicative of, for example, a certain population, a disease state, or a propensity for a disease state.

"Polymorphism" or "genetic variant" means a substitution, inversion, insertion, or deletion of one or more nucleotides at a genetic locus, or a translocation of DNA from one genetic locus to another genetic locus. In one aspect, polymorphism means one of multiple alternative nucleotide sequences that may be present at a genetic locus of an individual and that may comprise a nucleotide substitution, insertion, or deletion with respect to other sequences at the same locus in the same individual, or other individuals within a population. An individual may be homozygous or heterozygous at a genetic locus; that is, an individual may have the same nucleotide sequence in both alleles, or have a different nucleotide sequence in each allele, respectively. In one aspect, insertions or deletions at a genetic locus comprises the addition or the absence of from 1 to 10 nucleotides at such locus, in comparison with the same locus in another individual of a population (or another allele in the same individual). Usually, insertions or deletions are with respect to a major allele at a locus within a population, e.g. an allele present in a population at a frequency of fifty percent or greater.

18. "Polynucleotide" or "oligonucleotide" are used interchangeably and each mean a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moities, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al., Molecular Cloning, Second Edition (Cold Spring Harbor Laboratory, New York, 1989), and like references.

19. "Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of from 14 to 36 nucleotides.

20. "Sample" means a quantity of material from a biological, environmental, medical, or patient source in which detection or measurement of target nucleic acids is sought. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention. "Sample" is also used to refer to the solution derived from any of the above sources as it processed in preparation for further testing or assays.

21. "Solid support", "support", and "solid phase support" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. Microarrays usually comprise at least one planar solid phase support, such as a glass microscope slide.

22. "Specific" or "specificity" in reference to the binding of one molecule to another molecule, such as a labeled target sequence for a probe, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecules in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak non-covalent chemical interactions, such as Van der Waal forces, hydrogen bonding, base-stacking interactions, ionic and hydrophobic interactions, and the like, dominate the interaction of the molecules.

23. "siRNA" refers to small interfering RNAs, which also include short hairpin RNA (shRNA) (Paddison et al., Genes & Dev. 16: 948-958, 2002), that are capable of causing interference and can cause post-transcriptional silencing of specific genes in cells, for example, mammalian cells (including human cells) and in the body, for example, mammalian bodies (including humans). The phenomenon of RNA interference is described and discussed in Bass, *Nature,* 411:428-29, 2001; Elbashir et al., *Nature,* 411:494-98, 2001; and Fire et al., *Nature,* 391:806-11, 1998, wherein methods of making interfering RNA also are discussed. The siRNAs based upon the sequence disclosed herein (for example, GenBank Accession Nos. NM_001336 and NM_013230 for CTSZ and CD24, respectively) is typically less than 100 base pairs ("bps") in length and constituency and preferably is about 30 bps or shorter, and can be made by approaches known in the art, including the use of complementary DNA strands or synthetic approaches. The siRNAs are capable of causing interference and can cause post-transcriptional silencing of specific genes in cells, for example, mammalian cells (including human cells) and in the body, for example, mammalian bodies (including humans). Exemplary siRNAs according to the invention could have up to 30 bps, 29 bps, 25 bps, 22 bps, 21 bps, 20 bps, 15 bps, 10 bps, 5 bps or any integer thereabout or therebetween. According to the invention, siRNA having different sequences but directed against CTSZ or CD24 can be administered concurrently or consecutively in any proportion, including equimolar proportions.

24. The term "miRNA" refers to microRNA, a class of small RNA molecules or a small noncoding RNA molecules, that are capable of causing interference, inhibition of RNA translation into protein, and can cause post-transcriptional silencing of specific genes in cells, for example, mammalian cells (including human cells) and in the body, for example, mammalian bodies (including humans) (see, Zeng and Cullen, *RNA,* 9(1):112-123, 2003; Kidner and Martienssen *Trends Genet,* 19(1):13-6, 2003; Dennis C, *Nature,* 420(6917):732, 2002; Couzin J, *Science* 298(5602):2296-7, 2002). Previously, the miRNAs were known as small temporal RNAs (stRNAs) belonged to a class of non-coding microRNAs, which have been shown to control gene expression either by repressing translation or by degrading the targeted mRNAs (see Couzin J, *Science* 298(5602):2296-7, 2002), which are generally 20-28 nt in length (see Finnegan et al., *Curr Biol,* 13(3):236-40, 2003; Ambros et al., RNA 9(3): 277-279, 2003; Couzin J, *Science* 298(5602):2296-7, 2002). Unlike other RNAs (for example, siRNAs or shRNAs), miRNAs or stRNAs are not encoded by any microgenes, are generated from aberrant (probably double-stranded) RNAs by an enzyme called Dicer, which chops double-stranded RNA into little pieces (see Couzin J, *Science* 298(5602): 2296-7, 2002). According to the invention, miRNA having different sequences but directed against CTSZ or CD24 can be administered concurrently or consecutively in any proportion, including equimolar proportions.

25. "$T_m$" is used in reference to "melting temperature." Melting temperature is the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation. $T_m=81.5+0.41$ (% G+C), when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr., Biochemistry 36, 10581-94 (1997)) include alternative methods of computation which take structural and environmental, as well as sequence characteristics into account for the calculation of $T_m$.

B. DESCRIPTION OF THE GENERAL METHOD OF THE INVENTION

FIGS. 1A and 1B show steps in practicing the method of the invention in embodiments that employ a single-stranded target probe and a single-stranded, hairpin detection probe (1A), and a single-stranded hairpin target probe and a single-stranded detection probe (1B).

In both embodiment, the object of the method is to detect the presence of a target sequence in a DNA or RNA polynucleotide analyte contained in a sample, such as polynucleotide analytes 20, 22 in FIGS. 1A and 1B, respectively, having the 5' to 3' orientation shown. The target sequence typically includes a region of at least 10-12 bases, typically 10-20 bases or more, one or a few bases of particular interest, such as point or deletion mutations, or single-nucleotide polymorphisms (SNPs). That is, the nucleotide base or bases of interest may include only one or a few bases, but the target sequence for probe-binding specificity will include an additional several bases adjacent the target bases of interest. As will be discussed further below, the sample may contain a single analyte, e.g., one polynucleotide species with one target region of interest, or multiple targets contained one or more polynucleotide species. The operation of the method for detection of multiple target regions is generally referred to as a multiple mode.

For purposes of illustration, the method that will be described with respect to FIGS. 1A and 1B is intended to detect a single SNP target sequence that includes a GT sequence characteristic of a SNP sequence of interest, as shown in the figures. Details for carrying out SNP detection are given in Example 1 and 2. This GT sequence is part of a target sequence that may include 10-20 known-sequence bases that terminate and connect with 3' end of the GT sequence bases.

The detection method involve first, mixing a sample containing the target polynucleotide with a target probe having a sequence capable of hybridizing with the portion of the analyte target sequence just downstream of the target base(s) or interest, in this case, terminating with a 3'-end adenosine (A) base that can hybridize to the thymidine (T) base of the GT sequence in the target sequence. In the method illustrated in FIG. 1A, a target probe is a single-stranded DNA probe 24, and in the method illustrated in FIG. 1B, the target probe is a single-stranded probe 26, in thus case, a hairpin probe having a stem-loop duplex structure, where the targeting complementary sequence in the hairpin probe (the sequence that is complementary to the analyte target sequence) preferably includes bases within the hairpin loop of the probe, such that the target probe can form a longer duplex region with the analyte target sequence than with can by internal hairpin formation, kinetically favoring formation of the duplex over the hairpin structure. The mixing of an analyte polynucleotides and a target probe is carried out under conditions effective to hybridize the target probe to the complementary region of the analyte target sequence, to form an analyte/probe duplex complex.

In the next step in the method, the duplex complex is reacted in the presence of a polymerase and a selected one to three of four possible nucleotide triphosphates, to add a defined number of target-directed nucleotide bases to the probe's 3' end. In the embodiments shown, a single cytidine triphosphate (CTP) is added. This reaction will add a cytidine base at the complementary G base in the target GT target sequence and, assuming that site does not contain an adjacent G base, the reaction will terminate after the addition of the single base to the probe. The modified probe having a 3-end added C base is shown at 24' in FIG. 1A and at 26' in FIG. 1B.

More generally, the reaction is carried out in the presence of one to three selected nucleotide triphosphates, ensuring that the polymerase reaction will terminate when the first base in the analyte that does not have a complementary NTP in the reaction mixture is encountered. Thus, for example, if the reaction contained ATP, CTP, and GTP, the polymerase addition reaction would continue to add nucleotides to the 3'-end of the probe as long as a contiguous T, G, or C base were present in the target, but would terminate when the first A base was encountered in the target sequences.

Figure 11:
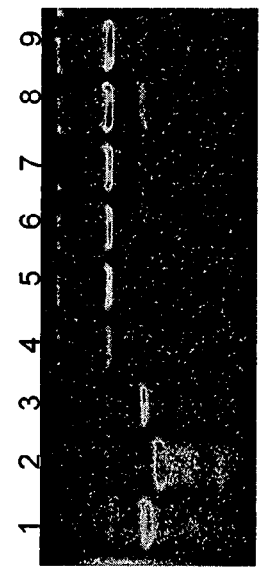
FIG. 11 illustrates steps in producing multiple modified probes from a single target. The figure shows a linear increase of circular probes (ligation products of extended probes and detection probes) by including cycles of denature, annealing and extension. 1. Target probe, 2. Synthetic target, 3. Detection probe, 4. 4-cycle extension-ligation-Exo, 5. 10-cycle extension-ligation-Exo, 6. 15-cycle extension-ligation-Exo, 7. 25-cycle extension-ligation-Exo, 8. 35-cycle extension-ligation-Exo, 9. 50-cycle extension-ligation-Exo.

As will be described further below with respect to FIGS. 2B and 11, the target probe is preferably added in substantial molar excess, e.g., 10-100 times molar excess, and the probe-modification reaction is carried out over several cycles with thermal cycling to enhance the molar ratio of analyte to modified probe.

Following one or more rounds of nucleotide addition to the target probe, the modified probe is now reacted with a detection probe having a 3'-end sequence that is complementary to a 3' end sequence of the modified target probe, in the presence of a ligase enzyme, to ligate the modified target probe with the detection probe as shown in the lower frames FIGS. 1A and 1B. Where the target probe is a single stranded probe, as in FIG. 1A, the detection probe is a single-stranded hairpin probe, such as probe 28 having a 3' overhang that is complementary to modified 3' end of the target probe. The ligation product formed by binding of the modified target probe and detection probe through their complementary 3'-end sequences, and ligation of target probe's 3'-end to the 5' end of the detection probe is shown at 32. Where the target probe is a single-stranded hairpin probe, as in FIG. 1B, the detection probe may be a single- or double-stranded polynucleotides, such as a single-stranded probe 30 having a 3' end that is complementary to the modified 3' end of the target hairpin probe. The two-probe ligation product formed by binding of the modified target probe and detection probe through their complementary 3'-end sequences, and ligation of target probe's 5'-end to the 3' end of the detection probe is shown at 34.

The target-sequence of interest can now be detected by the presence of the two-probe ligation product, since the ligation product will form only after analyte-directed modification of the target probe and base-paired interaction of the modified target probe with the detection probe. Details for carrying out these steps are given in Example 1 and 2. Various method for detecting the ligation product are described below, and generally involve amplifying the ligation product and detecting the amplification products. Thus, the method provides two steps at which the target sequence can be amplified for detection purposes: first, through amplification of target probe by thermal cycling in the presence of a molar excess of target probe to produce multiple modified probes from a single target, and secondly, by amplification of all or a portion of the final two-probe ligation product.

C. PROBE COMPONENTS AND OPERATION OF SPECIFIC EMBODIMENTS

Figure 2A:
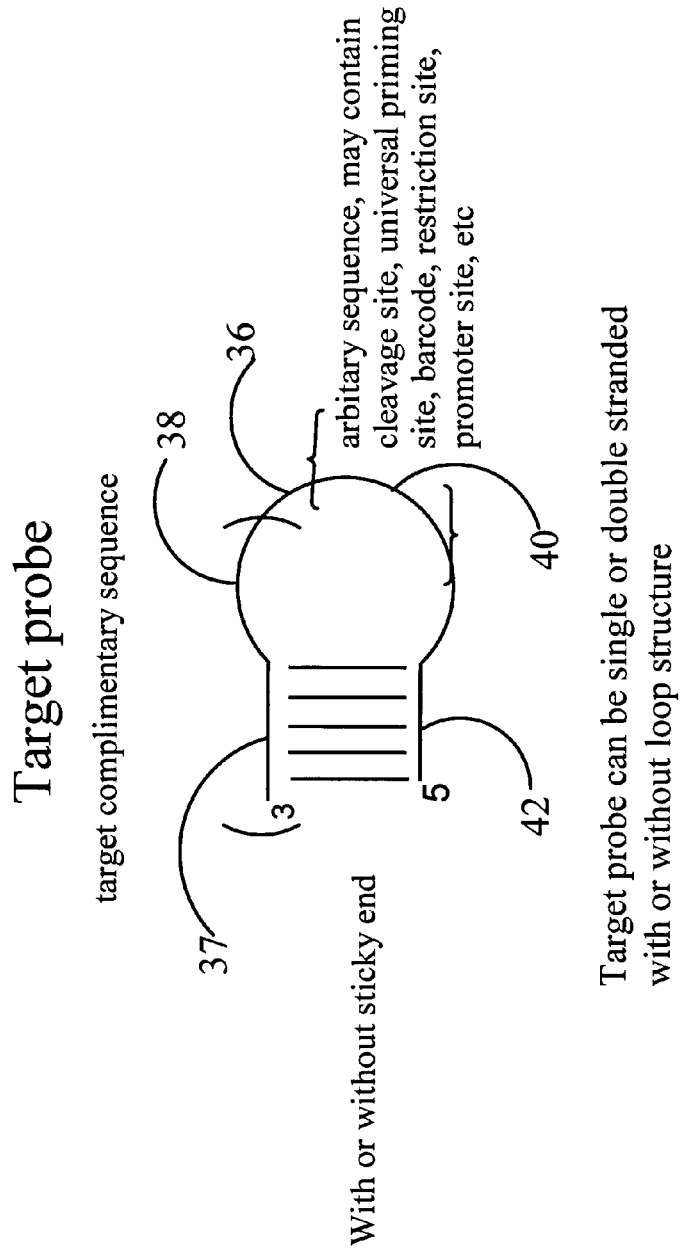

FIG. 2A shows a single-stranded hairpin probe 36 for use in the method illustrated in FIG. 1B. As seen, the probe includes complementary-sequence portions 37, 42 at the probe's 3' and 5' ends, respectively, responsible for the probe's secondary structure. The 3' end of the probe may have an overhang, e.g., one-base overhang, as shown in FIG. 1B, or may be flush with the probe's 5'-end, it is understood that the probe modification step will either extend an existing probe overhang or create an overhang where the unmodified probe has flush ends. The region of the probe designed to hybridize to the target sequence is indicated by parentheses at 38 in the figure, and includes portion 37 and additional sequences within the probe hairpin. As indicated above, region 38 is typically 10-20 bases or more in length. The hairpin region of the probe, indicated at 40, may also include additional arbitrary or functional sequences, such as one or more restriction sites, a universal priming site, a promoter site, or barcode sequence for probe identification.

Figure 2B:
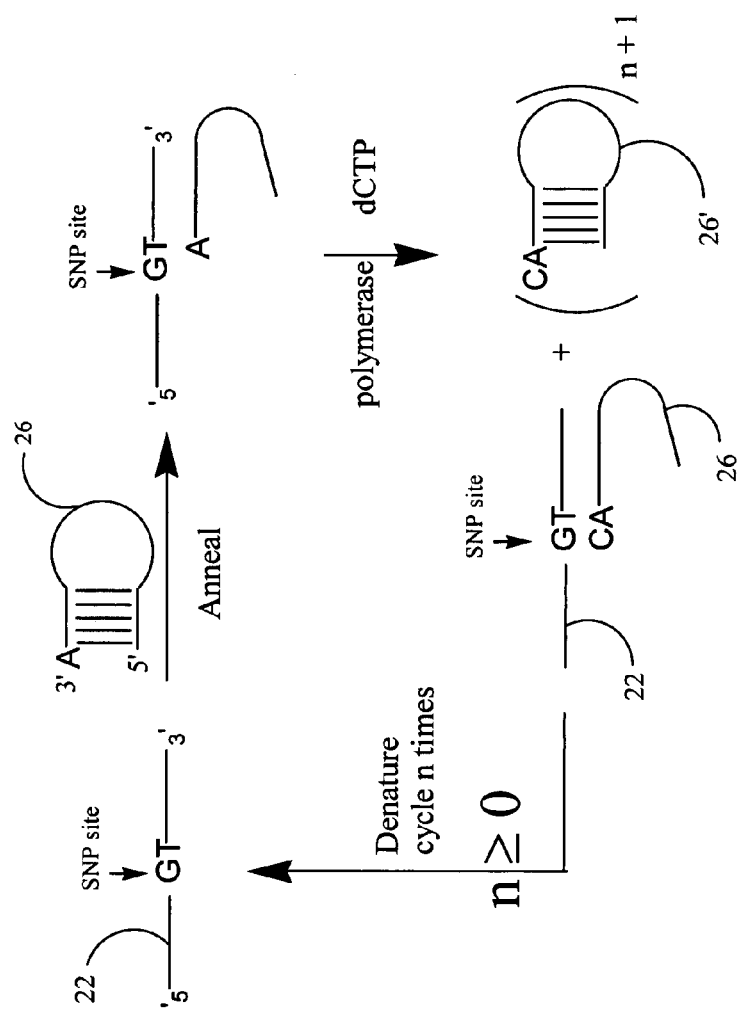

FIG. 2B illustrates the probe modification and amplification reactions in the method, as outlined above with respect to FIG. 1B. In this example, hairpin probe 26 is added is substantial molar excess with respect to the target analyte 22, which has a GT-containing SNP site to be detected. Initially, a portion of the hairpin probe will anneal with the analyte, forming relatively stable duplex structures, relative to the probe's internal duplex structure, by virtue of the longer region of duplex formed in the probe/analyte complex. In the presence of polymerase, and a selected one-three nucleotides, in this case, dCTP, the target probe is extended at its 3' end, in this case by a single C base to form a two-base (CA) overhang in the probe. Details for carrying out these steps are given in Example 1.

The reaction mixture is now heated above the probe/analyte's duplex Tm, to release the modified probe, and cooled, to allow new probe to hybridize to the analyte. With each of these thermal cycles, the probe in the analyte complex is extended at its 3' end, as above. This thermal cycling may be repeated until substantially all of the probe in the reaction mixture has been modified. The polymerase employed in the reaction is typically a heat-stable DNA polymerase, such as a *T. aquaticus* (Taq) polymerase. Details for carrying out these steps are given in Example 3.

FIG. 2C shows a hairpin, single-stranded detection probe 44, similar to probe 28 described with respect to FIG. 1A. The probe includes complementary-sequence portions 46, 48 at the probe's 5' and 3' ends, respectively, responsible for the probe's secondary structure. The 3'-end of the probe has an overhang 50, e.g., a two-six base overhang that is complementary to the 3'-end overhang in the modified target probe, and the base structure needed for complementary-base interaction with the modified target probe. Except overhang sequence 50, the detection probe 44 may also include additional arbitrary or functional sequences, such as one or more restriction sites, a universal priming site, a promoter site, or barcode sequence for probe identification.

Figure 2D:
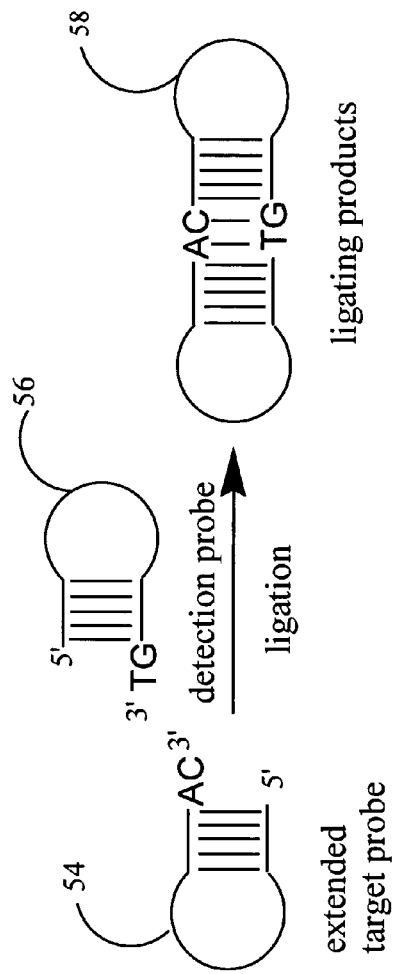

FIG. 2D illustrates the ligation reaction in which target and detection probes 54, 56, respectively, with their complementary 3'-end overhangs are brought together and ligated to form a two-probe ligation product 58. The ligation enzyme is typically T4 DNA ligase, and ligation is carried out under standard conditions, e.g., RT for 20 minutes. The detection probe and ligase enzyme are typically added to the reaction mixture after modified probe produced. Where, as here, both the modified probe and detection probe are hairpin structures, the resulting ligation product is a circular, single-stranded fragment that contains the target-probe sequences and detection probe sequences, and detection probe sequences include additional elements, such as a promoter element, for synthesizing copies of the ligation product. In this embodiment, the method may also include treating the final reaction mixture with an exonuclease, such as Exonuclease I and Exonuclease III, to remove non-circularized (unreacted) probes and targets. The reaction is thereby substantially enriched for the desired two-probe ligation product(s). Details for carrying out these steps are given in Example 1.

Figure 2E:
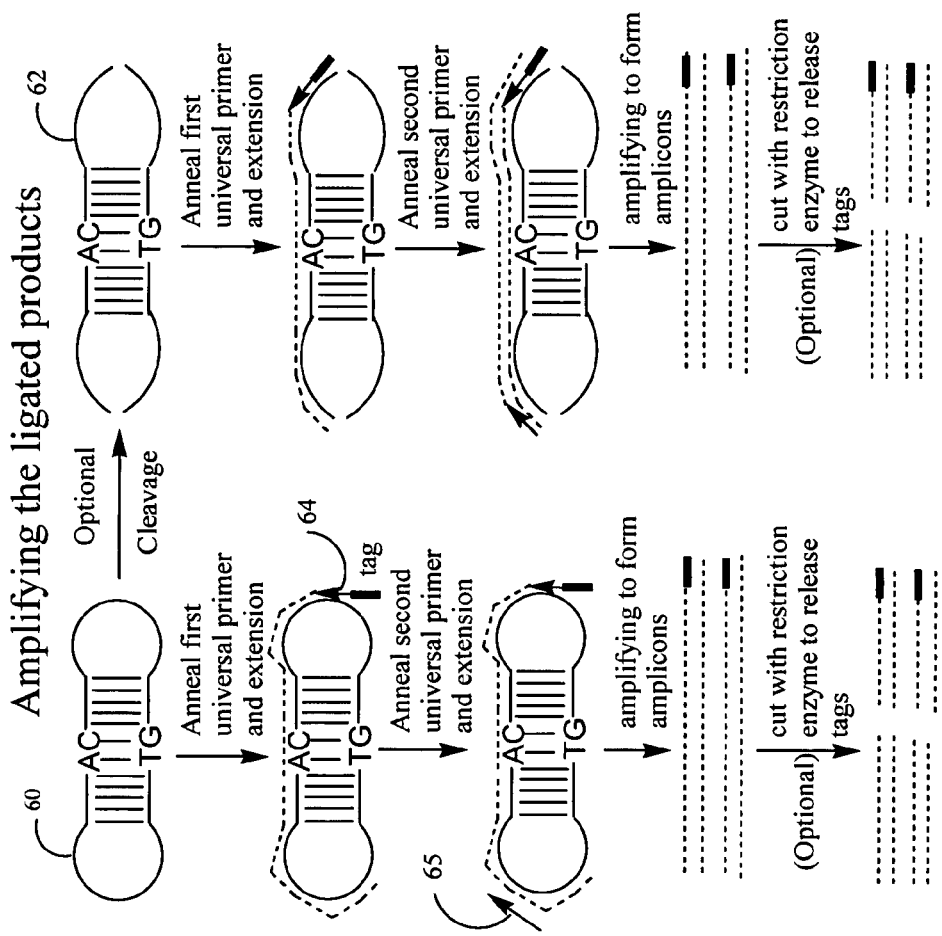

FIG. 2E illustrates a PCR method for amplifying the two-probe ligation product, for purposes of detecting the ligation product. As seen, amplification may be carried out on either the intact, circularized product, shown at 60, or on the same product after cleavage to break the product into separate linear strands, such as strand 62. The product (either intact or fragment) is annealed with a first universal primer 64 that carries a detectable label, as indicated, and subject to one round of primer-initiated polymerization. A second universal primer 65 is used to produce an opposite-strand, as indicated, yielding a double-stranded copy of a portion of the ligation product. This double-stranded copy is then PCR amplified, conventionally, employing a universal labeled primer, e.g., fluorescent-labeled primer, to label one of the two amplified strands. Details for carrying out PCR reactions are given in Example 5.

Figure 2F:
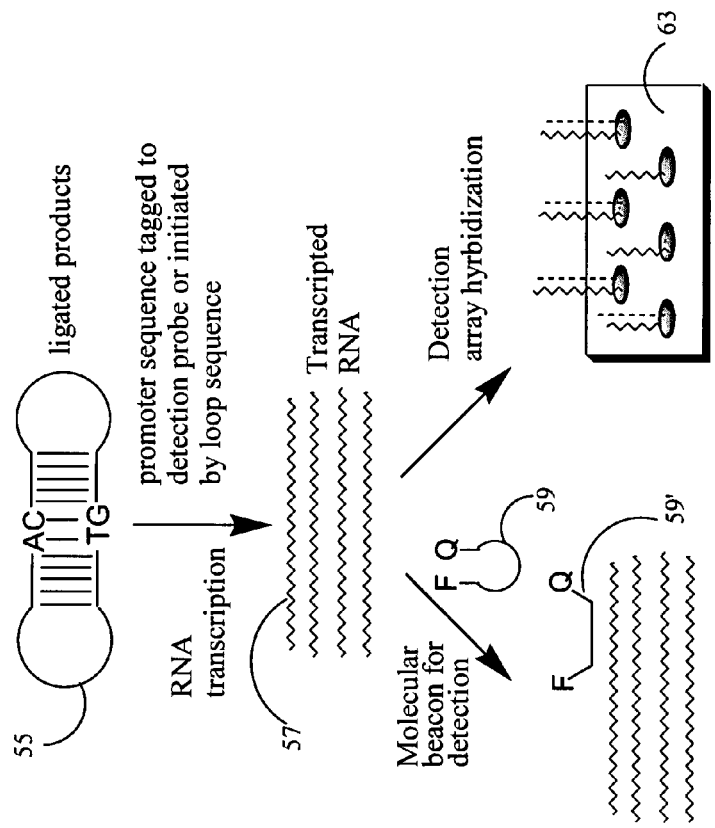

FIG. 2F shows another method for amplifying the target-sequence contained in a two-probe ligation product 55. In this example, ligation product 55 includes, in either detection probe or target probe, a promoter, such as a T7 promoter sequence, or the hairpin itself, that can be used to generate RNA transcripts, as shown at 57, that include the target sequence, when the product is reacted with a suitable transcriptase, e.g., T7 RNA polymerase, in the presence of NTPs. The presence of the amplified transcripts can be detected in solution phase using a conventional molecular-beacon probe 59, capable of reacting with the transcript sequence to produce a detectable (unquenched) signal. Alternatively, the transcripts can be synthesized in the presence of a suitable fluorescent-labeled ribonucleotide triphosphate, and detected by attachment to an oligo-probe array 63, as discussed below. The latter approach has the advantage of being able to detect a very large number of analyte sequences in a single multiplexed reaction format. Details for carrying out transcription reactions are given in Example 8.

Other methods for amplifying all or portions of the two-probe ligation product are suitable and contemplated herein. One such method, known as rolling circle amplification (RCA) employs a single primer, e.g., universal primer, for linear amplification, and a pair of primers for exponential amplification, as described, for example, in U.S. Pat. No. 5,854,033 by Lizardi et al. Details for carrying out rolling circle amplification are given in Example 5.

Figure 2G:
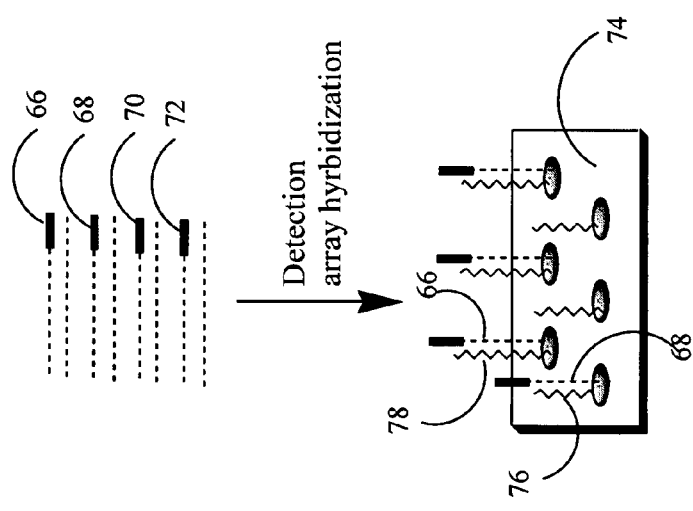

FIG. 2G shows a reaction scheme involving amplified, labeled double-stranded fragments having four different target-specific sequences 66, 68, 70, 72. The amplified fragments are added to a gene chip 74 having attached single-stranded probes, such as probes 76, 78 designed to hybridize to sequence-specific regions of the labeled fragments, such as fragments 68, 66, respectively. After reacting the labeled fragments with chip probes under hybridization conditions, the presence or absence of each target sequence can be determined by the presence of absence of labeled probe at each know-sequence region of the chip. It will be appreciated that is actual practice, the method can be used for multiplexed detection of hundreds or thousands of different target sequences, e.g., some large number of SNPs in the human genome associated with various disease states. In this application, where a large number of different-sequence target and detection probes are used, probes having hairpin structures are advantageous in reducing the degree of cross-probe hybridization that can occur.

Figure 3:
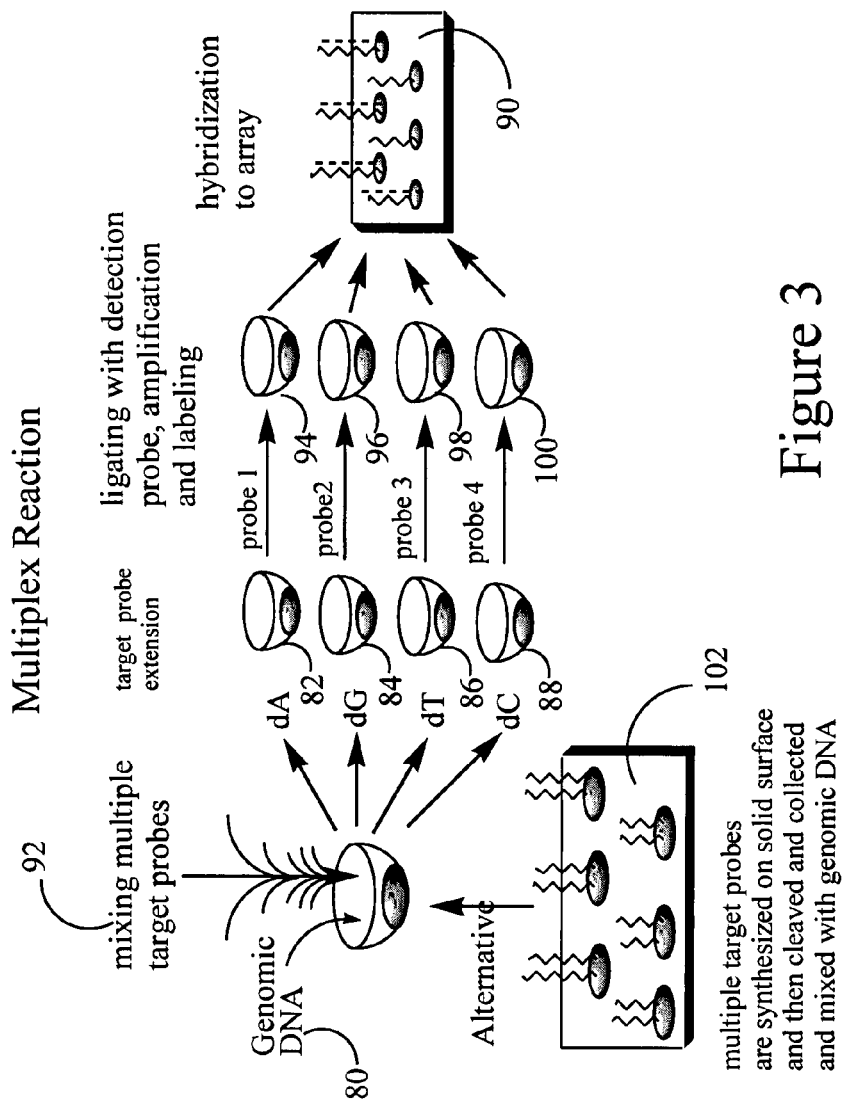
FIG. 3 illustrates the method of the invention carried out with a four-color detection scheme for detecting for multiple analyte sequences of interest.

To further expand the capacity of the method for detecting large numbers of analyte sequences, FIG. 3 depicts a multiplex assay design according to some embodiments of the present invention. A sample 80 contains a plurality of different target sequences to be detected, e.g., genomic DNA 80. To the sample is added a plurality of target probes 92 to promote hybridization between target probes and target sequences to form hybridization complex. The hybridization complex is divided into four aliquots 82, 84, 86, 88. Each aliquot is added a different single nucleotide triphosphate, 82 with dATP, 84 with dGTP, 86 with dTTP, 88 with dCTP. Following repeating hybridization and extension in the presence of a polymerase to produce modified probes in each aliquot, different detection probe can be added to each aliquot (probe 1 for 82, probe 2 for 84, probe 3 for 86, probe 4 for 88) to promote ligation between detection probe and modified probes to form ligation products in vessels 94, 96, 98, 100. The ligation products in each vessel are then amplified with different labeled universal primers or transcribed with different labeled NTP to produce labeled amplicons. The labeled amplicons from each vessel are mixed and then detected by hybridization with probes attached on DNA array 90. Decoding the array involves scanning the array, noting the fluorescence signal associated with each array region, and confirming the presence of a given sequence terminating at a given nucleotide base. The plurality of target probes 92 can be made by mixing individual target probes, or synthesis of each target probe from a solid surface such as array 102. Cleaving target probes attached on array 102 forms a mixture of plurality of target probes 92. Some details for carrying out multiplex reactions are given in Example 5.

Figure 4:
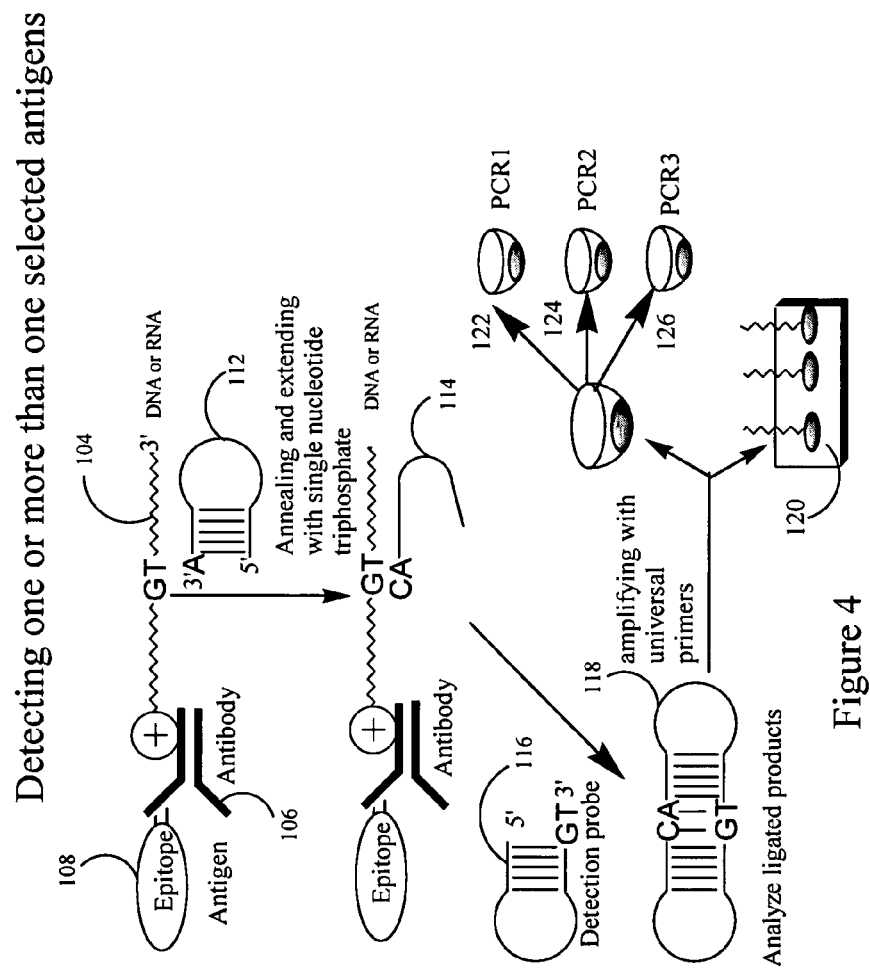
FIG. 4 shows a proteomics probe for use in detecting one or more than one selected proteins, where probe detection is carried out in accordance with the present invention.

FIG. 4 illustrates the use of the method for amplifying and detecting a polynucleotide 104 having a defined sequence and which itself serves as a marker for an assay reagent, in this case, an antibody 106 specific against a given antigen 108. For example, the antigen may be one of a large number of antigens arrayed on a solid surface, in a proteomics study to identify antigens with specific epitope characteristics. Likewise, the study may involve a plurality of antibodies with different epitope specificities, each carrying a reagent-specific polynucleotides with its own target sequence. As can be appreciated, the polynucleotide markers provide a virtually unlimited number of different markers that can be individually detected, e.g., for use in a large proteomics array.

After binding of the antibody reagents to the solid surface such as beads attached with analytes, and washing the beads to remove unbound reagent, the beads are exposed to a reaction mixture containing target probes, such as probe 112, where each probe has a targeting sequence designed for hybridization to one of the plurality of different-sequence polynucleotide markers bound to the beads. The probes are now extended, e.g., by a single base (C), as shown, to yield modified probes, such as probe 114, each having with a distinctive targeting sequence, but with the same single base extension. As above, the reaction may be carried out with a molar excess of the target probes, allowing probe expansion by several rounds of thermal cycling.

Following probe extension, the target probes are reacted with a common-sequence detection probe, such as probe 116, in the presence of ligase, to form two-probe ligation products, such as the circular product 118. These products, which can represent a large number of different-sequence markers, are detected by one of the methods above, typically involving forming amplified, labeled fragments of a portion of the ligation product containing the marker-specific sequence, and decoding of the labeled fragments on an oligonucleotide array 120. In this way, the presence or absence of any given marker sequence bound to an antigen in the original antigen beads can be ascertained by the binding of a labeled probe to the corresponding oligonucleotide on the oligo array 120. Alternatively, the ligation products can be amplified with universal primers and then divided into one or more aliquots 122, 124, 126, and amplifying each aliquot with antigen specific primers to detect the presence of each antigen.

D. METHOD AND KIT FOR RNA DETECTION

Figure 5:
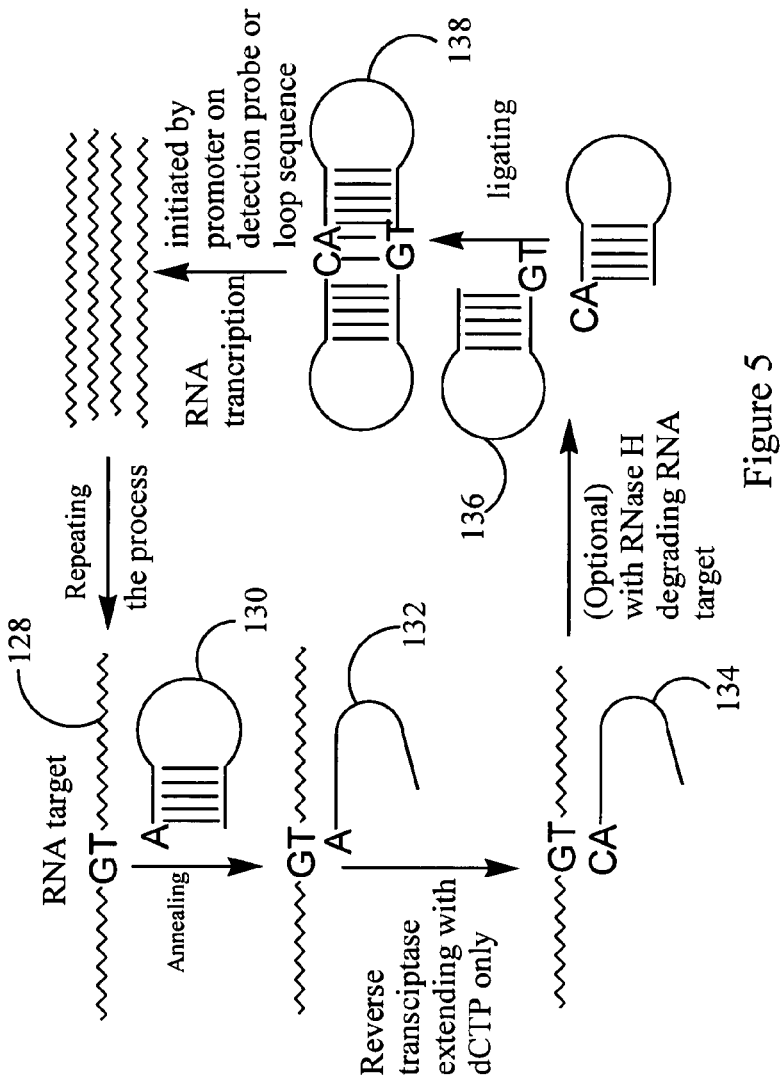
FIG. 5 illustrates steps in detecting an RNA analyte in accordance with an embodiment of the invention.

This section examines specific applications of the invention for amplification and detecting sequence-specific RNA targets. Details for carrying out these methods are given in Example 6, 7, 8. With reference to FIG. 5, an RNA polynucleotide analyte having a target sequence terminating at a GT sequence is shown at 128. As discussed above, the target sequence may be 10-20 bases or more in length, but where the critical base(s) of interest are those at or near the 3' end of the target sequence, e.g., the two GT bases in the figure. As with the more generally described method above, the first step in the method is extension of a target probe, such as hairpin probe 130, by hybridization of the targeting region of the probe to the RNA analyte in the presence of a selected one to three of four dNTPs, in this case, dCTP, to form an analyte/probe complex 132. Probe modification is then carried out in the presence of one-to-three selected dNTPS, e.g., dCTP, as shown, in the presence of a reverse transcriptase, such as MMLV (Invitrogen), capable of RNA to DNA transcription, to yield the extended target probe 134. As indicated, the reaction mixture may be treated with an RNase, such as RNaseH, to degrade analyte RNA in the duplex.

The detection probe employed in the method is preferably a hairpin probe 136 having a 3'-overhang complementary to the extended target probe overhang, and an internal promoter sequence, such as a T7 promoter, capable of supporting RNA transcription in the presence of a RNA polymerase, such as T7 polymerase. Reaction of the two probes with probe ligation in the presence of a ligase thus yields a circular single-stranded two-probe ligation product 138 having an internal promoter sequence followed by a probe-specific sequence. Transcripts are produced in the presence of RNA polymerase. The resulted transcripts can be used as targets to repeat the amplification process. For detection, a molecular beacon probe can be introduced into the reaction mixture. The molecular beacon probe such as 59 will hybridize with transcripts to produce detectable signal as described in FIG. 2F.

E. METHOD AND KIT FOR MULTIPLEX MICRO RNA DETECTION micro RNAs (miRNAs) typically comprise single-stranded, endogenous oligoribonucleotides of roughly 22

(18-25) bases in length that are processed from larger stem-looped precursor RNAs by Dicer. MicroRNA with roughly 22 bases in length is not long enough to accommodate two primers for amplification by using PCR or NASBA. Therefore there has been little reliable technology available for miRNA quantitation (Allawi et al., Third Wave Technologies, RNA. 2004 July; 10(7):1153-61). Northern blotting has been used but results are not quantitative (Lagos-Quitana et al., 2001, Science, 294 (5543), 853-854). Many miRNA researchers are interested in monitoring the level of the miRNAs at different tissues, at the different stages of development, or after treatment with various chemical agents. However, the short length of miRNAs has their study difficult.

Figure 6:
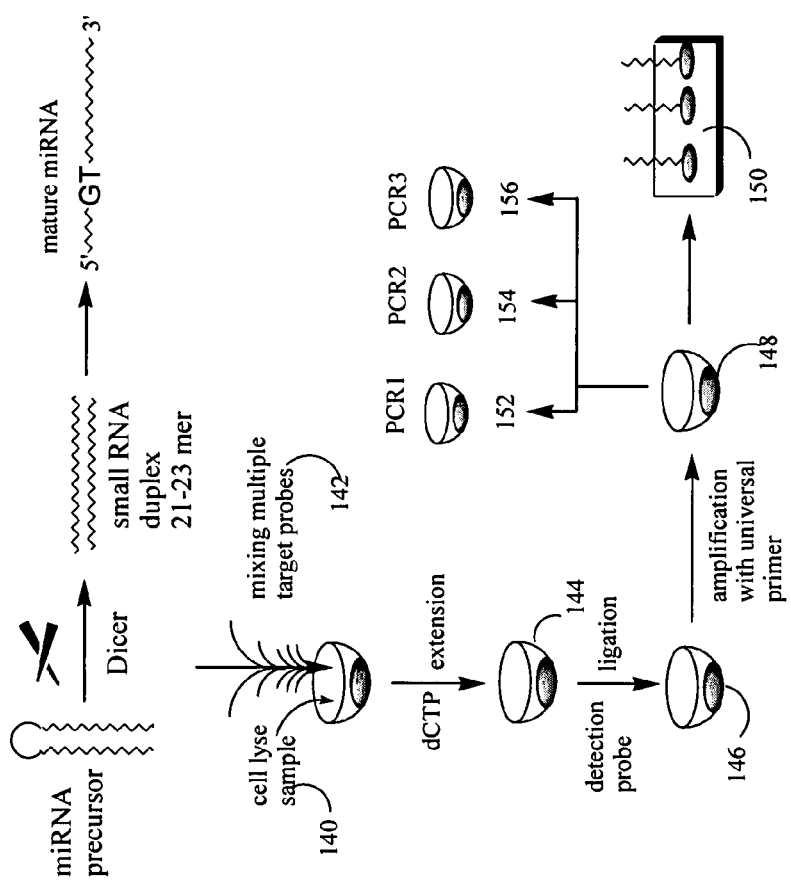
FIG. 6 illustrates steps in multiplex miRNA detection in accordance with the invention.

FIG. 6 depicts a multiplex assay design according to some embodiments of the present invention. A sample 140 contains a plurality of different micro RNA target sequences to be detected, e.g., a cell lyse sample 140. To the sample is added a plurality of target probes 142 and one to three of the four dNTPS, in this case dCTP. Following hybridization and extension in the presence of a polymerase to produce modified probes in the reaction vessel 144, one or more detection probes can be added to the reaction vessel 144 to promote ligation between detection probe and modified probes to form ligation products in reaction vessel 146. The ligation products are then amplified with universal primers to produce amplicons in the reaction vessel 148. The amplicons are divided into one or more aliquots, 152, 154, 156 respectively. Each aliquot is then amplified with specific primers. Detection of the amplification product in each aliquot indicates the presence of the specific miRNA. Alternatively, the ligation products are amplified with incorporation of detection labels and amplicons are then detected by hybridizing with probes attached on solid surface 150. Decoding the array involves scanning the array, noting the fluorescence signal associated with each array region, and confirming the presence of a given microRNA.

In embodiment, the methods of the invention permit the detection and identification of microorganisms, e.g., pathogens infecting mammals. Thus, the invention can be used, e.g., to identify the particular strain of a virus that is infecting a human subject, e.g., the particular strain of human immunodeficiency virus, or papilloma virus (HPV), among others. Strains of microorganisms often differ from each other in a few nucleotides, whereas the remaining of their genomes is identical. Thus, probes can be made to recognize the conserved regions and to identify the particular variable nucleotide(s).

For example, a wide variety of infectious diseases can be detected by the process of the present invention. Typically, these are caused by bacterial, viral, parasite, and fungal infectious agents. The resistance of various infectious agents to drugs can also be determined using the present invention.

The present invention is also useful for detection of drug resistance by infectious agents. For example, vancomycin-resistant *Enterococcus faecium*, methicillin-resistant *Staphylococcus aureus*, penicillin-resistant *Streptococcus pneumoniae*, multi-drug resistant *Mycobacterium tuberculosis*, and AZT-resistant human immunodeficiency virus can all be identified with the present invention.

Genetic diseases can also be detected by the process of the present invention. This can be carried out by prenatal or post-natal screening for chromosomal and genetic aberrations or for genetic diseases. Examples of detectable genetic diseases include: 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia. Tay-Sachs Disease, thalassemia, Klinefelter Syndrome, Huntington Disease, autoimmune diseases, lipidosis, obesity defects, hemophilia, inborn errors of metabolism, and diabetes.

Cancers which can be detected by the process of the present invention generally involve oncogenes, tumor suppressor genes, or genes involved in DNA amplification, replication, recombination, or repair. Examples of these include: BRCA1 gene, p53 gene, APC gene, Her2/Neu amplification, Bcr/AB1, K-ras gene, and human papillomavirus Types 16 and 18. Various aspects of the present invention can be used to identify amplifications, large deletions as well as point mutations and small deletions/insertions of the above genes in the following common human cancers: leukemia, colon cancer, breast cancer, lung cancer, prostate cancer, brain tumors, central nervous system tumors, bladder tumors, melanomas, liver cancer, osteosarcoma and other bone cancers, testicular and ovarian carcinomas, head and neck tumors, and cervical neoplasms.

In the area of environmental monitoring, the present invention can be used for detection, identification, and monitoring of pathogenic and indigenous microorganisms in natural and engineered ecosystems and microcosms such as in municipal waste water purification systems and water reservoirs or in polluted areas undergoing bioremediation. It is also possible to detect plasmids containing genes that can metabolize xenobiotics, to monitor specific target microorganisms in population dynamic studies, or either to detect, identify, or monitor genetically modified microorganisms in the environment and in industrial plants.

The present invention can also be used in a variety of forensic areas, including for human identification for military personnel and criminal investigation, paternity testing and family relation analysis, HLA compatibility typing, and screening blood, sperm, or transplantation organs for contamination.

In the food and feed industry, the present invention has a wide variety of applications. For example, it can be used for identification and characterization of production organisms such as yeast for production of beer, wine, cheese, yogurt, bread, etc. Another area of use is with regard to quality control and certification of products and processes (e.g., livestock, pasteurization, and meat processing) for contaminants. Other uses include the characterization of plants, bulbs, and seeds for breeding purposes, identification of the presence of plant-specific pathogens, and detection and identification of veterinary infections and in animal breeding programs.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

Example 1

Target Probe Extension Based on Allele Specific Hybridization

This example demonstrates that a target probe with self-complementary sequence (hairpin structure), under hybridization condition, form a hybridization complex with target sequence. If the 3' ended base of the target probe is complementary to the allele specific nucleotide on target sequence, under polymerization condition, one or several nucleotides will be added to the 3' end of the target probe based on the type or number of nucleotides added. Such extension would lead to 3' end sequence of the target probe complementary with 3' end sequence of detection probe to make ligation between two probes possible. Hairpin probes named as Oct-25-2005-R was designed and ordered from Integrated DNA Technology for testing the extension reaction. Two synthetic target sequences were designed to test allele specific extension. One of the target sequences named as RS1389629-G is fully complementary to the target probe. The other target sequences named as RS1389629-C is also complementary with the target probe, but not with the last base at 3' end of the target probe. Two detection probes are designed named as Oct25-2005 F and Oct-25-2005-2F respectively. Oct25-2005 F is complementary to target sequence adjacent to the extended target probe. Ligation between Oct25-2005 F and extended target probe is template dependent ligation. Oct-25-2005-2F does not complementary to target sequence. Ligation between Oct-25-2005-2F and extended target probe is template independent.

Target probe sequence with hairpin structure Oct-25-2005-R:

(SEQ ID NO: 1)
5'-phosphate-GGCTCCATACGGACTCCCACAGTGAGGAGCC 3'

Detection probe sequence with hairpin structure for template dependent ligation Oct25-2005 F:

(SEQ ID NO: 2)
5'-phosphate-ATCCCATTATCCTCCATGCAATGGGATCCA-3'

Detection probe sequence with hairpin structure for template independent ligation Oct-25-2005-2F:

(SEQ ID NO: 3)
5'-phosphate

CCGTGTGCTATATGTTAGTATTGGACACACACGGCCA 3'

Target sequences RS1389629-G fully complementary to target probe:

(SEQ ID NO: 4)
5'AATATATGGAGGATAATGGGATCCAGGCTCCTCACTGTGGGAGAAGAA

GTT 3'-target with allele G

Target sequences RS1389629-C complementary to target probe, but not the last base at the 3' end of target probe:

(SEQ ID NO: 5)
5'AATATATGGAGGATAATGGGATCCACGCTCCTCACTGTGGGAGAAGAA

GTT 3'-target with allele-C

Four parallel extension reactions (30 μl) were performed as follows with one of these two target sequences which are different from each other by only single nucleotide (SNP):
1) Target probe extension reaction without detection probe present: target DNA (100 μM) 1 μl and hairpin probe Oct-25-2005-R (100 μM) 3 μl were added to the extension reaction mix which containing: 0.5 μl of 10 mM dGTP, 0.5 μl of 10 mM dTTP (10 mM), 3 μl of 10× Stoffel buffer (100 mM Tris-HCl, pH 8.3, 100 mM KCl), 0.5 μl of 10 U/μl AmpliTag DNA Polymerase Stoffel Fragment (Application Biotechnology), 4.8 μl of 25 mM MgCl2.
2) Target probe extension reaction with detection probe present: target DNA (100 μM) 1 μl, hairpin probe Oct-25-2005-R (100 μM) 3 hairpin detection probe Oct-25-2005-F or Oct-25-2005-2F (100 μM) 3 were added to the extension reaction mix which containing: 0.5 μl of 10 mM dGTP, 0.5 μl of 10 mM dTTP (10 mM), 3 μl of 10× Stoffel buffer (100 mM Tris-HCl, pH 8.3, 100 mM KCl), 0.5 μl of 10 U/μl AmpliTag DNA Polymerase Stoffel Fragment (Application Biotechnology), 4.8 μl of 25 mM MgCl2.

Hairpin target probes Oct-25-2005-R were extended on a Thermal Cycler (MJ Research) programmed as:
Pre denature at 95° C. for 2 min
10 cycles of 95° C. for 1 min, 60° C. 1 min
70° C. for 5 min
95° C. for 3 min
After reaction, samples were incubated at 4° C.

DNA loading buffer (0.05% bromophenol blue, and 30% sucrose) was added to samples. Samples were then electrophoresed on a 20% denaturing polyacrylamide gel. Each hairpin probe was loaded onto the gel, which represents the hairpin detection probe.

Figure 7:
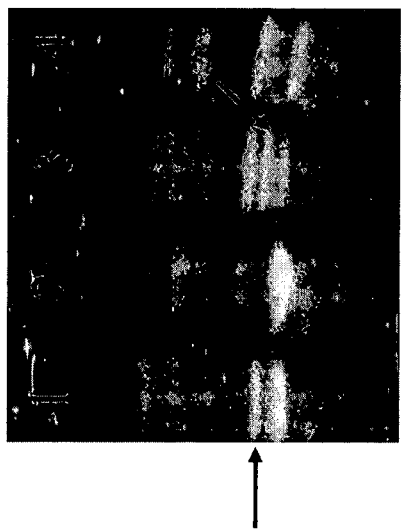
FIG. 7 illustrates steps in producing modified probes. Separation of probes after limited base-extension from 3' end of the target probes on a 20% denaturing polyacrylamide gels (arrows indicate the base added target probes). 1. probe R+F, target RS1389629-G; 2. probe R+F, target RS1389629-C; 3. probe R+2F, target RS1389629-G; 4. probe R+2F, target RS1389629-C.

Results: the results indicate a 3-nucleiotide stick-end (-TGG) formed at 3' end of the hairpin extension probe Oct-25-2005-R (FIG. 7) after hybridized to target RS1389629-G which contains the complementary SNP to that presents in the probe 3' end, but not in the other lanes in which target RS1389629-C presented.

Ligation Reaction Between Detection Probe and Extended Target Probe to Form Circular Ligated Products:
1) template dependent ligation: 4 μl of aliquots from extension reaction 1) were pipetted out and added into 16 μl ligase mix [2 μl of T4 DNA ligase buffer (500 mM Tris-Hcl, pH 7.5 10 mM ATP), 0.8 μl of T4 DNA ligase (3 U/μl, Promega), 0.5 μl hairpin detection probe Oct-25-2005-F, 12.7 μl of water]. The ligation reaction was incubated for 6 hrs at 16° C.
2) template independent ligation: 4 μl of aliquots from extension reaction 2) were pipetted out and added into 16 μl ligase mix [2 μl of T4 DNA ligase buffer (500 mM Tris-Hcl, pH 7.5 10 mM ATP), 0.8 μl of T4 DNA ligase (3 U/μl, Promega),), 0.5 μl hairpin detection probe Oct-25-2005-2F, 13.2 μl of water]. The ligation reaction was incubated for 6 hrs at 16° C.

Exonuclease Treatment to Remove Linear Templates or Probes, but not Circular Ligated Products:
5 μl of aliquots from the ligation reaction was mixed with 5 μl of Exonuclease mix prepared by mixing (per reaction) 1 μl of 10× Exo I buffer (New England Biolabs); 0.5 μl of Exonuclease I (E. coli) at 20 u/μl (New England Biolabs); 0.5 μl of Exonuclease III (E. coli) at 100 u/μl (New England Biolabs); and 3 μl of water. The reactions were then incubated for 3 hours at 37° C.

Figure 8:
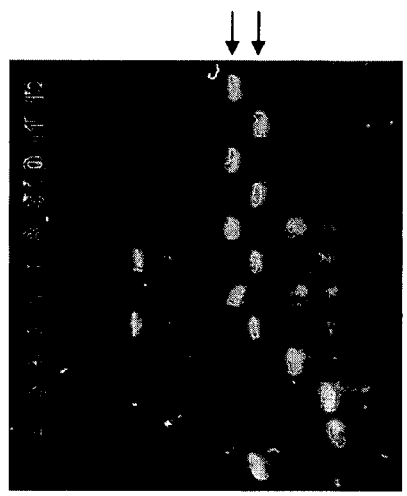
FIG. 8 illustrates steps to ligate modified probes and detection probes, and exonuclease to digest any linear probes and targets. A 20% denaturing polyacrylamide gel shows the ligation and Exonuclease digestion results. Arrows indicate the ligation of 3' end extended target probe and detection probe—circularized probes. Gel separation was performed 1.5 hours. 1. RS1389629-G; 2. Oct25-2005 F; 3. Oct25-2005 R; 4. Oct25-2005 2F; 5, 7. ligation F+R; 6, 8. Ligation 2F+R; 9, 11. ligation-Exo (F+R); 10, 12. ligation-Exo (2F+R)

5 μl of each Exo digested product was then subjected to electrophoresis on a 20% denaturing polyacrylamide gel, and the circularized products were visualized by SYBR Green I (Roche) staining and U.V. light (FIG. 8).

Example 2

Target Probe Adjacent to SNP Site is Extended by Single Nucleotide for SNP Detection This example described that target probe adjacent to SNP site is extended by single nucleotide for SNP detection. Target probe hybridizes to target sequences located adjacent to SNR site. Target probe with only correct base added at its 3' end is able to ligate with detection probe to form a ligated circular product. The SNP is identified according to the type of nucleotide added. Reaction between extended target probe and detection probe is sticky end ligation. 3' end of the target hairpin probe annealing to target sequence extends one nucleotide from the 3' end of the hairpin sequence, if only correct single nucleotide triphosphate and DNA polymerase present in the reaction. With further cycles of denaturing, annealing and extension, the number of based-extended target probes will increase in the reaction mixture. Under the presence of DNA ligase, detection hairpin probe, which have a two-nucleotide overhangs at its 3' end and complementary to the stick ends of the extended target probe overhangs, will ligate with extended target probe to form a circular dumbbell product. The circular dumbbell product is exonuclease resistant. Thus, after exonuclease digestion, detection ligated circular product associating with the type of nucleotide added will help to identify type of SNP.

Four synthetic target sequences were designed and synthesized according to the alignment of *Glycine max* receptor-like kinase RHG1 Gene sequences. "/" indicates the SNP location. The segments of genomic DNA sequence containing four SNPs are listed as following:

SNP1 (SEQ ID NO. 6)
GAACAACGTTAACCCATGTTGTTTTTGTTTCTCTTATGTGTGTGGAGCC

TTGTTGTGCTCCCCTCATGCGTGAGGCCAGTTTTGTGTGAAGATGAAGGT

TGGGATGGAGTGGTTGTGACAGCATCAAACCTCTTAGCACTTGAAGCTTT

CAAGCAAGAGTTGGC/TTGATCCAGAAGGGTTCTTGCGGAGCTGGAATGA

CAGTGGCTATGGAGCTTGTTCCGGAGGTTGGGTTGGAATCAAGTGTGCT

SNP2 (SEQ ID NO. 7)
TGATCCAGAAGGGTTCTTGCGGAGCTGGAATGACAGTGGCTATGGAGCTT

GTTCCGGAGGTTGGGTTGGAATCAAGTGTGCTC/AAGGGACAGGTTATTG

TGATCCAGCTTCCTTGGAAGGGTTTGAGGGGTCGAATCACCGACAAAATT

GGCCAACTTCAAGGCCTCAGGAAGCTTAGTCTTCATGATAACCAAATTGG

TGGTTCAATCCCTTCAACTTTGGGACTTCTTCCCAACCTTAGAGG

SNP3 (SEQ ID NO. 8)
CCTTTACCAGCTAGCCTAACTCACTCATTTTCTCTCACTTTTCTTTCTCT

TCAAAATAACAATCTTTCTGGCTCCCTTCCTAACTCTTGGGGTGGGAATT

CCAAGAATGGCTTCTTTAGGCTTCAAAATTTGATCCTAGATC/AATAACT

TTTTCACTGGTGACGTTCCTGCTTCTTTGGGTAGCTTAAGAGAGCTCAAT

GAGATTTCCCTTAGTCATAATAAGTTTAGTGGAGCTATACCAAATGAAA

SNP4 (SEQ ID NO. 9)
CTGCTTTTCTGCCTGATCAGAAAGAGATCAACATCTAAGGCCGGGAACGG

CCAAGCCACCGAGGGTAGAGCGGTCACTTATGAGGACAGAAAAAGGAGTC

CCTCCAGTTGCTGG/CTGGTTGATGTTGAAGCAGGTGGGGAGGCTGGAGG

GGAACTAGTCCATTTTGATGGACCAATGGCTTTTACAGCTGATGATCTCT

TGTGTGCAACAGCTGAGATCATGGGAAAGAGCACCAATGGAA

Synthetic targets, target hairpin probes and detection probes are listed as following:

SNP 1 synthetic target (RHG-SNP1-template-C-40)
(SEQ ID NO: 10)
5'-CTTTCAAGCAAGAGTTGG C TGATCCAGAAGGGTTCTTGCG-3'

Target probe for SNP1 (RHG-SNP1-probe-35)
(SEQ ID NO: 11)
5'-phosphate-GATCCAGAATCTTGCGCAAGAACCCTTCTGGATCA-3'

Detection probe for SNP1 (Univ-CT)
(SEQ ID NO: 12)
5'-phosphate-CCGTGTGCTACATCTAAGTATAGGACTATGTTATATT

GGGCACACGGCT-3'

SNP 2 synthetic target (RHG-SNP2-template-C-41)
(SEQ ID NO: 13)
5'-GTTGGAATCAAGTGTGCT C AGGGACAGGTTATTGTGATCCA-3'

Target probe for SNP2 (RHG-SNP2-probe-38)
(SEQ ID NO: 14)
5'-phosphate-GGGACAGGATCTTGCGCGGATCACAATAACCTGTCCCT-3'

Detection probe for SNP2 (Univ-CA)
(SEQ ID NO: 15)
5'-phosphate-CCGTGTGCTACATCTAAGTATAGGACTATGTTATATT

GGGCACACGGCA-3'

SNP 3 synthetic target (RHG-SNP3-template-C-38)
(SEQ ID NO: 16)
5'-AATTTGATCCTAGAT C ATAACTTTTTCACTGGTGACGT-3'

Target probe for SNP3 (RHG-SNP3-probe-46)
(SEQ ID NO: 17)
5'-phosphate-TAACTTTTTCACATCTTGCGCGGCACGTCACCAGTGA

AAAAGTTAT-3'

Detection probe for SNP3 (Univ-CT)
(SEQ ID NO: 12)
5'-phosphate-CCGTGTGCTACATCTAAGTATAGGACTATGTTATATT

GGGCACACGGCT-3'

SNP 4 synthetic target (RHG-SNP4-template-C-39)
(SEQ ID NO: 18)
5'-AGTCCCTCCAGTTGCTG C TGGTTGATGTTGAAGCAGGTG-3'

Target probe for SNP 4 (RHG-SNP4-probe-41)
(SEQ ID NO: 19)
5'-phosphate-GGTTGATGATCTTGCGCGGCAGCCTGCTTCAACATCA

ACCA-3'

Detection probe for SNP4 (Univ-CA)
(SEQ ID NO: 15)
5'-phosphate-CCGTGTGCTACATCTAAGTATAGGACTATGTTATATT

GGGCACACGGCA-3'

Each SNP reaction was carried out separately.

Probe Annealing and Extension: The reactions were set up in 200 μl PCR tubes in a 15 μl reaction volume containing 2.5 units AmpliTag DNA Polymerase Stoffel Fragment (Application Biotechnology), 10 mM Tris-HCl (pH 8.3), 10 mM KCl, 4 mM MgCl$_2$, 0.15 mM dGTP. Reactions contained 5 μM extension probes and 1.5 μM target DNA. The cycling program consisted of initial denaturation at 95° C. for 3 min, followed by 50 cycles at 95° C. for 30 s, annealing and extension at 58° C. for 1 min. And a final extension at 72° C. for 5 min.

Ligation Reaction: For each 30 μl reaction to be run, 15 μl of ligation mix was prepared as follows: 3 μl of 10 times T4 DNA ligase buffer (500 mM Tris-Hcl, pH 7.5 10 mM ATP), 1.2 μl of T4 DNA ligase (3 U/μl, Promega), 1 μl of 100 μM Univ-probe and 9.8 μl water.

15 μl of ligation mix was added to the 15 μl extension reaction. Ligation reaction was performed on a Thermal Cycler (MJ Research) at 16° C. for 1 hr, and at 37° C. for 20 min.

Exonuclease reaction to remove the linear targets or probes: 6 μl of aliquots from the ligation reaction was mixed with 4 μl of Exonuclease mix prepared by mixing (per reaction) 0.5 μl of Exonuclease I (*E. coli*) (20 u/µl, New England Biolabs); 0.5 µl of Exonuclease III (*E. coli*) (100 u/µl, New England Biolabs); and 3 µl of water. The reactions were then incubated for 3 hours at 37° C.

Figure 10:
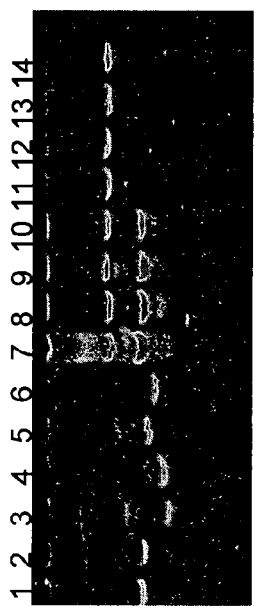
FIG. 10 illustrates steps for SNP detection. Detect individual SNP using hairpin probes and soybean synthetic targets by detecting extension and ligation products. 1. Univ-CA, 2. Univ-CT, 3-6, extension of SNP1, 2, 3, 4 probe; 7-10, SNP1, 2, 3, 4 probe extension—ligation; 11-14, circularized probes: SNP1, 2, 3, 4 probe extension—ligation—Exo digest.

5 µl of each Exo digested product was then subjected to electrophoresis on a 20% denaturing polyacrylamide gel, and the circularized products were visualized by SYBR Green I (Roche) staining and U.V. light (FIG. 10)

Bands at lane 11, 12, 13, 14 are circular dumbbell products after exonuclease treatment. The results have clearly demonstrated the feasibility of current technology for SNP detection.

Example 3

Sensitivity Test by Increasing the Amount of Extended Target Probe Based on Thermal Cycling the Probe Extension Reaction Probe annealing and extension with cycling the reaction 1, 10, 15, 25, 35, 50 times respectively: The reactions were set up in 200 µl PCR tubes in a 15 µl reaction volume containing 2.5 units AmpliTaq DNA Polymerase Stoffel Fragment (Application Biotechnology), 10 mM Tris-HCl (pH 8.3), 10 mM KCl, 4 mM MgCl$_2$, 0.15 mM dGTP. Reactions contained 5 µM extension probes and 1.5 µM target DNA. The cycling program consisted of initial denaturation at 95° C. for 3 min, followed by 50 cycles at 95° C. for 30 s, annealing and extension at 58° C. for 1 min. And a final extension at 72° C. for 5 min.

The amount of extended products produced with increasing number of cycles is estimated based on ligation reaction product with detection probe after exonuclease treatment. Results from FIG. 11 (lane 4 to lane 9) clearly demonstrated that increasing cycling probe annealing and extension reaction increases ligated products.

Example 4

The Specificity of Nucleotide Addition to Extend the Target Probe

Figure 12:
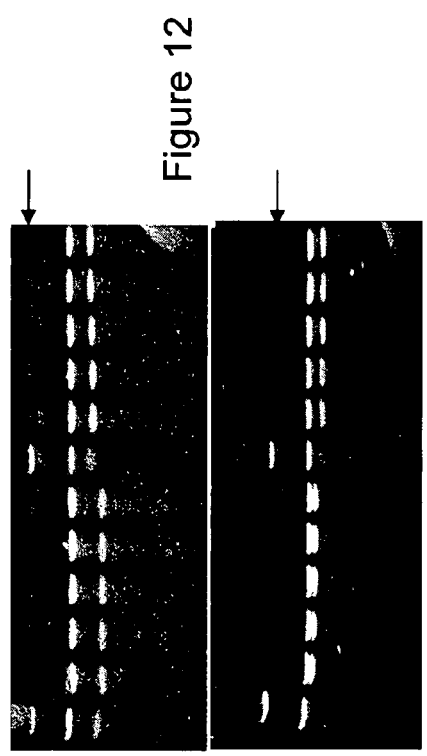
FIG. 12. illustrates specificity of target probe modification. Limitation of target probe extension and ligation by adding dXTP.

The reactions were carried out as described in example 2 except using less amount of targets (0.1 µM). 24 reactions were conducted: 4 reactions for each SNP with individual nucleotide added, and two negative controls without nucleotide added or without target template exist (Table 1). Target probe hybridized with target sequence adjacent to a base of C in the target. One of four nucleotide triphosphates was added to extend the target probe separated. The extended products were evaluated based on ligation reaction with detection probe after exonuclease treatment. Experimental data shows that only correct base dGTP added is able to extend the target probe to form circular ligated products (FIG. 12).

TABLE 1

Hairpin probe extended on an oligonucleotide target, and then ligased with a detection hairpin probe

| | Tube | | | | | | | |
|---|---|---|---|---|---|---|---|---|
| | 1 | 2 | 3 | 4 | 5 | 6 | 7 | 8 |
| Target probe | RHG-SNP1-probe-35 | RHG-SNP1-probe-35 | RHG-SNP1-probe-35 | RHG-SNP1-probe-35 | RHG-SNP1-probe-35 | RHG-SNP1-probe-35 | RHG-SNP2-probe-38 | RHG-SNP2-probe-38 |
| Target | RHG-SNP1-template-C-40 | RHG-SNP1-template-C-40 | RHG-SNP1-template-C-40 | RHG-SNP1-template-C-40 | RHG-SNP1-template-C-40 | | RHG-SNP2-template-C-41 | RHG-SNP2-template-C-41 |
| dXTP | dGTP | dCTP | dTTP | dTTP | | dGTP | dGTP | dCTP |
| Detection probe | Univ-CT | Univ-CT | Univ-CT | Univ-CT | Univ-CT | Univ-CT | Univ-CA | Univ-CA |

| | Tube | | | | | | | |
|---|---|---|---|---|---|---|---|---|
| | 9 | 10 | 11 | 12 | 13 | 14 | 15 | 16 |
| Target probe | RHG-SNP2-probe-38 | RHG-SNP2-probe-38 | RHG-SNP2-probe-38 | RHG-SNP2-probe-38 | RHG-SNP3-probe-46 | RHG-SNP3-probe-46 | RHG-SNP3-probe-46 | RHG-SNP3-probe-46 |
| Target | RHG-SNP2-template-C-41 | RHG-SNP2-template-C-41 | RHG-SNP2-template-C-41 | | RHG-SNP3-template-C-38 | RHG-SNP3-template-C-38 | RHG-SNP3-template-C-38 | RHG-SNP3-template-C-38 |
| dXTP | | dTTP | dTTP | dTTP | dGTP | dCTP | dTTP | dATP |
| Detection probe | Univ-CA | Univ-CA | Univ-CA | Univ-CA | Univ-CA | Univ-CA | Univ-CA | Univ-CA |

| | Tube | | | | | | | |
|---|---|---|---|---|---|---|---|---|
| | 17 | 18 | 19 | 20 | 21 | 22 | 23 | 24 |
| Target probe | RHG-SNP3-probe-46 | RHG-SNP3-probe-46 | RHG-SNP4-probe-41 | RHG-SNP4-probe-41 | RHG-SNP4-probe-41 | RHG-SNP4-probe-41 | RHG-SNP4-probe-41 | RHG-SNP4-probe-41 |
| target | RHG-SNP3-template-C-38 | | RHG-SNP4-template-C-39 | RHG-SNP4-template-C-39 | RHG-SNP4-template-C-39 | RHG-SNP4-template-C-39 | RHG-SNP4-template-C-39 | |
| dXTP | | dGTP | dGTP | dCTP | dTTP | dATP | | dGTP |

TABLE 1-continued

Hairpin probe extended on an oligonucleotide target, and then ligased with a detection hairpin probe

| Detection probe | Univ-CA | Univ-CA | Univ-CT | Univ-CT | Univ-CT | Univ-CT | Univ-CT | Univ-CT |
|---|---|---|---|---|---|---|---|---|

Example 5

Multiplex SNP Reaction in a Single Tube

Multiplex SNP detection in a single tube was evaluated by using both synthetic target and total genomic DNA.

Synthetic DNA targets and hairpin probes used for this experiment were the same as listed in Example 2. Genomic DNA extracted and purified from two soybean breeding lines PI and Essex.

Multiplex SNP reactions were confirmed based on PCR by amplifying ligated circular products. PCR primers were designed to specially amplify each of ligated circular products. One primer corresponding to target probe is gene specific for each SNP. The other corresponding to detection probe is universal for four SNPs. Oligonucleotide primer sequences:

Universal Primer for Four SNPs (Univ-Primer2)

```
5' ATGTTATATTGGGCACAC 3'        (SEQ ID NO: 20)

Gene specific primer for SNP1
CCAGAAGGGTTCTTG                 (SEQ ID NO: 21)

Gene specific primer for SNP2
CAGGTTATTGTGATC                 (SEQ ID NO: 22)

Gene specific primer for SNP3
CTTTTTCACTGGTGAC                (SEQ ID NO: 23)

Gene specific primer for SNP4
GTTGATGTTGAAGCAG                (SEQ ID NO: 24)
```

Multiplex extension reaction: 30 μl multiplex reaction containing 5 μM of each of the four extension probes, 100 nM each of the four synthetic DNA targets or 50 ng of soybean genomic DNA, 5 units AmpliTaq DNA Polymerase Stoffel Fragment (Application Biotechnology), 10 mM Tris-HCl (pH 8.3), 10 mM KCl, 4 mM MgCl$_2$, 0.15 mM dGTP. The thermal conditions were as follow: initial pre-denature at 95° C. for 3 min, 95° C. denaturing for 30 s and 58° C. annealing and extension for 1 min, repeat 50 times, plus a final extension at 72° C. for 5 min.

Multiplex ligation reaction: a aliquot of 6 μl of extension reaction was mixed with 24 μl of ligation cocktail containing 1.5 μl of each detection probe (100 μM Univ-CA and 100 μM Univ-CT), 3 μl of 10× T4 DNA ligation buffer, 2.5 μl of T4 DNA ligase (3 U/μl, Promega), and 18.5 μl of water. Ligation reaction was performed on a Thermal Cycler (MJ Research) at 16° C. for 20 min, 37° C. for 20 min.

Figure 13:
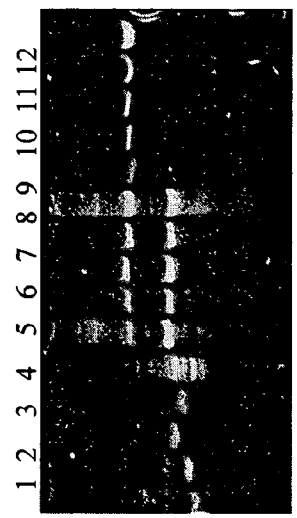
FIG. 13 illustrates steps for multiplex SNP detection. Detect multiplex SNPs using hairpin probes and soybean synthetic targets. 1-4, SNP1, 2, 3, 4 probe extension; 5, multiplex SNP extension; 6-9, SNP1, 2, 3, 4 probe extension—ligation; 10, multiplex SNP extension-ligation; 11-14, SNP1, 2, 3, 4 probe extension—ligation—Exo digest; 15, multiplex SNP extension-ligation-Exo digest.
Figure 9:
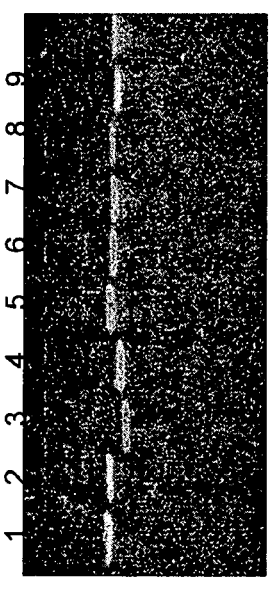
FIG. 9 illustrates probes and templates used. Gel identification of the synthetic targets and probes for multiplex SNP detection. 1. Univ-CT (49-mer), 2. Univ-CA (49-mer), 3. SNP1-probe (35-mer), 4. SNP2-probe (38-mer), 5. SNP3-probe (46-mer), 6. SNP4-probe (41-mer), 7. SNP1-template (40-mer), 8. SNP2-template (41-mer), 9. SNP3-template (38-mer), 10. SNP4-template (39-mer)

Multiplex exonuclease treatment to digest target and unliqated probes: 5 μl of aliquots from the ligation reaction was mixed with (per reaction) 0.25 μl of Exonuclease I (*E. coli*) (20 u/μl, New England Biolabs); 0.25 μl of Exonuclease III (*E. coli*) (100 u/μl, New England Biolabs), and incubated for 3 hours at 37° C. 0.5 μl of each of the exonuclease treated products were subjected to 20% denaturing polyarcylamide gel (FIG. 13).

1. PCR Specific Amplification of Circularized Probes to Verify the Specificity of Multiplex Reaction Product.

Figure 14:
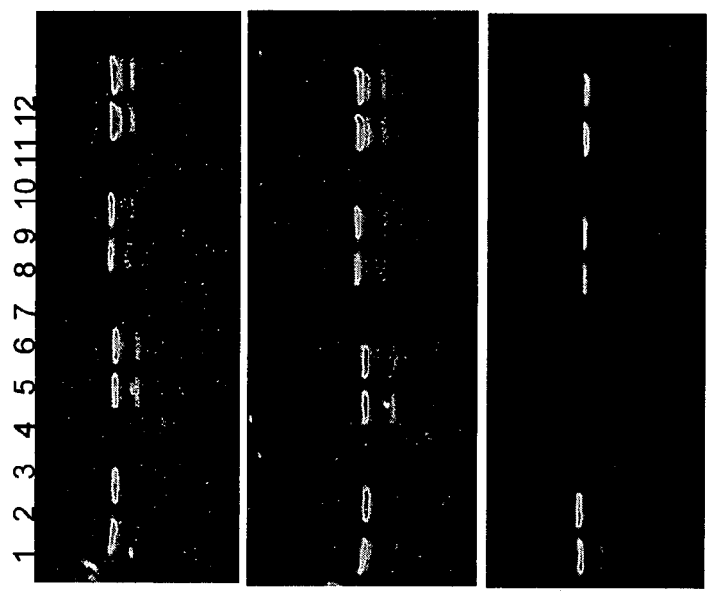
FIG. 14 illustrates steps of PCR amplification of multiplex SNP detection ligation products. PCR confirmation of the circularized probes from base-extended target probe and detection probe.

PCR was carried out on 1 μl of cleaned ligation product (product from synthetic template was diluted 100 times). Each primer pair was used to amplify multiplex reactions. Positive and negative controls were also included: 1) individual ligation product complementary to the primer, 2) multiplex ligation reactions, 3) multiplex reaction without primer complementary ligation product, 4) primer specific probes without ligation, 5) water only. The temperature profile was 95° C. for 3 min, 95° C. for 40S, 58° C. for 40S, 72° C. for 40S (35 cycles), and 72° C. for 5 min. All PCR products generated were ~70-80 bp in size (Table 2, FIG. 14)

TABLE 2

Detection of ligation using specific and universal primer amplification

| | Tube | | | | | |
|---|---|---|---|---|---|---|
| | 1 | 2 | 3 | 6 | 7 | 8 |
| Ligation product | SNP1 | SNP1, SNP2, SNP3, SNP4 | SNP2, SNP3, SNP4 | SNP2 | SNP1, SNP2, SNP3, SNP4 | SNP1, SNP3, SNP4 |
| sence primer | Univ-primer2 | Univ-primer2 | Univ-primer2 | Univ-primer2 | Univ-primer2 | Univ-primer2 |
| antisence primer | SNP1-special primer | SNP1-special primer | SNP1-special primer | SNP2-special primer | SNP2-special primer | SNP2-special primer |

| | Tube | | | | | |
|---|---|---|---|---|---|---|
| | 11 | 12 | 13 | 16 | 17 | 18 |
| Ligation product | SNP3 | SNP1, SNP2, SNP3, SNP4 | SNP1, SNP2, SNP4 | SNP4 | SNP1, SNP2, SNP3, SNP4 | SNP1, SNP2, SNP3 |
| sence primer | Univ-primer2 | Univ-primer2 | Univ-primer2 | Univ-primer2 | Univ-primer2 | Univ-primer2 |
| antisence primer | SNP3-special primer | SNP3-special primer | SNP3-special primer | SNP4-special primer | SNP4-special primer | SNP4-special primer |

2. Rolling Circle Amplification of Circularized Probes to Verify the Specificity of Multiplex Reaction Product.

Figure 15:
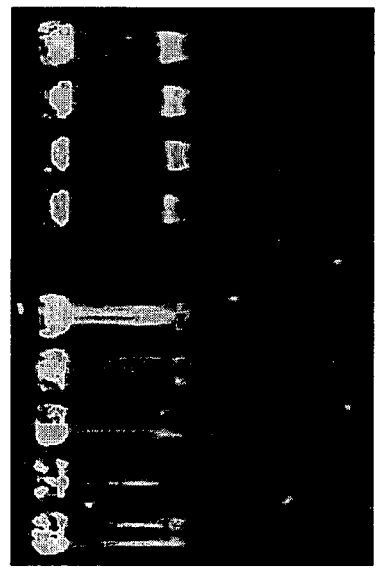
FIG. 15 illustrates steps of rolling circle amplification of ligation products. Rolling cycle amplification of circularized probes using circle specific antisence primer. 1. SNP1-ligation-Exo; 2. SNP2-ligation-Exo; 3. SNP3-ligation-Exo; 4. SNP4-ligation-Exo; 5. Multiplex SNPs (4 SNPs)-ligation-Exo; 6. Negative control; 7. SNP2-ligation-Exo, 200 time dilution; 8. SNP3-ligation-Exo, 200 time dilution; 9. SNP2-PI; 10. SNP2-Essex.

The ligation or ligation mixture was used for RCA. An aliquot of 1 μl of antisence primer specific to individual SNP-ligation product listed above was added. 10 μl reaction were heated to 70° C. and cooled to room temperature prior to the addition of 5 μl of RCA mix [800 μM dNTPs, 50 mM Tris-HCl (pH 8.3), 250 mM KCl, 7.5 mM MgCl$_2$, 0.8 μg/μl BSA, 10 U/μl of Phi 29 DNA polymerase], followed by incubation at 30° C. overnight. Reactions were terminated by incubation at 70° C. for 10 min. 1 μl of the reaction was subjected to 1.0% agarose gel electrophosis (FIG. 15).

Example 6

RNA and DNA Detection Using Current Technology

This example described a hairpin-shaped nucleic acid probe that is not only capable of detection of single nucleotide polymorphism, but also can be used to detect and quantify DNA and RNA in a complex mixture. In the condition of without target nucleic acid presence, hairpin probe 3' and 5' complementary sequences form a stable loop-stem conformation. Under denature condition, if target sequences is present, target hairpin probe will be able to hybridize to the target to form a hybridization complex. The hairpin structure in the target probe increases probe's hybridization specificity, as only probe-target hybridization complex that is thermodynamically more stable than the hairpin structure itself can form hybridization complex. After correct probe-target hybridization complex formed, nucleic acid polymerase will extend the probe along the target sequence to create a ligatable sticky ends. A detection probe with a sticky ends complementary to extended target probe's sticky ends, that is not hybridized to the target, can ligate with extended target probe to form a ligated product. If necessary, T7 promoter sequences can be included in detection probe. Adding the RNA polymerase and rXTPs to the ligated products will allow transcription to proceed until a desired (detectable) amount of RNA transcription product has accumulated. Alternatively, hairpin loop structure can be used to initiate RNA transcription. Synthetic RNA template was used to demonstrate the reaction.

```
Target probe sequence (RHG-SNP2-probe-38)
                                        (SEQ ID NO: 14)
5'-phosphate-

GGGACAGGATCTTGCGCGGATCACAATAACCTGTCCCT-3'

Detection probe sequence (Univ-CA)
                                        (SEQ ID NO: 15)
5'-phosphate-

CCGTGTGCTACATCTAAGTATAGGACTATGTTATATTGGGCACACGG

CA-3'

Synthetic RNA target sequence 1
(SNP2-Template-RNA-C)
                                        (SEQ ID NO: 25)
5 rGrUrGrCrUrCrArGrGrGrArCrArGrGrUrUrArUrUrGrUrGrA rUrCrCrArGrC-3

Synthetic RNA target sequence 2
(Maize-28s-probe-G)
                                        (SEQ ID NO: 26)
5'-PHOS/CGCCTGTCATCCTCCATGCTCGGGTCCCGACAGGCGT-3'
```

```
Synthetic RNA target sequence 3
(Maize-18S-template)
                                        (SEQ ID NO: 27)
5'-rGrCrArGrGrCrGrArUrCrCrUrCrCrArUrGrCrGrGrUrArAr UrUrUrGrCrGrCrGrCrCrUrGrCrU-3'

Synthetic RNA target sequence 4
(Maize-18S-probe-G)
                                        (SEQ ID NO: 28)
5'-PHOS/GCAGGCGATCCTCCATGCGGTAATTTGCGCGCCTGCT-3'

Detection probe with T7 promoter sequences
included (T7-hairpin-3)
                                        (SEQ ID NO: 29)
5/5Phos/CTCCCTATAGTGAGTCGTATTAATCCTCCATGCTAATACGAC

TCACTATAGGGAGCA 3'
```

Sense and antisense linear double stranded detection probe with T7 promoter sequences included,

```
Sense strand (T7-reverse-primer)
5'-PHOS/CTCCCTATAGTGAGTCGTATTA-3'    (SEQ ID NO: 30)

Antisense strand (T7-forward-primer)
5'-TAATACGACTCACTATAGGGAGCA-3'        (SEQ ID NO: 31)
```

RT Reaction

The reaction containing 1 μl SNP2-Template-RNA (25 μM), and 1.5 μl RHG-SNP2-probe-C (50 μM), was denatured by heating the reaction at 95° C. for 5 min followed by annealing (option) and adding 2.5 μl RT mix [0.5 μl DTT (0.1 M), 1 μl 5× First Strand Buffer, 0.25 μl dXTP (5 mM), 0.25 μM-MLV Reverse Transcriptase (200 u/μl), 0.5 μl H$_2$O], well mix the reaction by pipetting up and down and incubate at 37° C. for 8 min, 15 min, and then incubate the reaction at 65° C. for 15 min to inactive the Reverse Transcriptase Ligation At 37° C., 10 μl ligation mix [0.8 μl T4 DNA ligase (3 U/0), 1.5 μl 10× T4 ligation buffer, 1.0 μl Univ-CA (50 μM), 6.7 μl water] was added to the 5 μl RT reaction. The reaction was performed at 37° C. for 10, 20, 30 min respectively.

Exonuclease Treatment

Followed ligation reaction, 1 μl Exonuclease (ExoI: ExoIII=1:1) was added and incubated at 37° C. for 3 hr to remove linear RNA and DNA molecular.

Figures 16, 17, 18, 19:
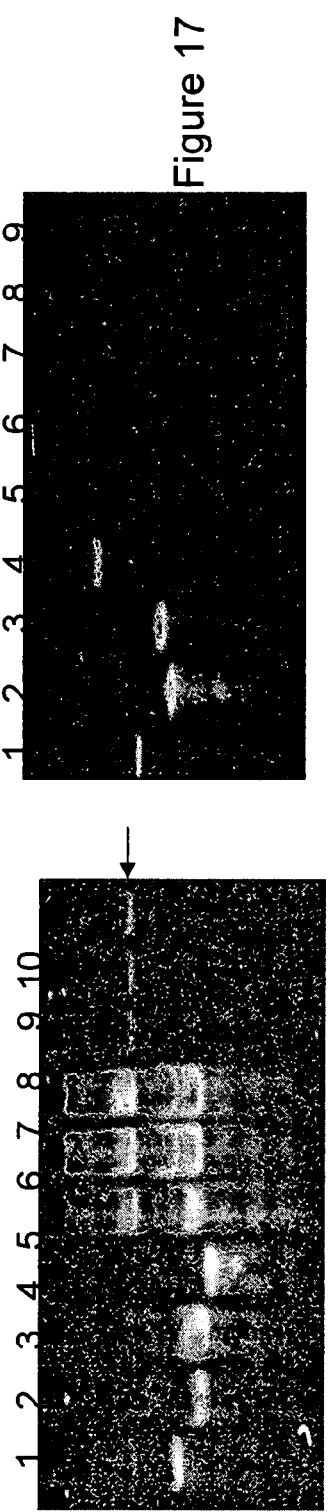
FIG. 16 illustrates steps of RNA detection. Detection of RNA by reverse transcription and ligation of extended target probe and detection probe. 1. Detection probe: Univ-probe-CA; 2. Target probe: RHG-SNP2-probe-38; 3. 8 min RT, arrow indicates extended target probe; 4. Synthetic RNA target; 5. 10 min ligation reaction; 6. 20 min ligation; 7. 30 min ligation; 8. 10 min ligation—Exo; 9. 20 min ligation—Exo; 10. 30 min ligation—Exo.
FIG. 17 illustrates steps of single tube isothermal amplification and detection of RNA. Single tube isothermal assay for synthetic RNA detection using hairpin target probes and detection probes. 1. Detection probe; 2. RNA target; 3. Target probe; 4. Single tube RT with dGTP-ligation, arrow indicates circularized probes; 5. Single tube RT with dATP-ligation; 6. Single tube RT with dTTP-ligation; 7. Single tube RT with dCTP-ligation; 8. No template; 9. NO RT.
FIG. 18 illustrates steps of transcription of ligation products. Single tube isothermal assay for total RNA detection using hairpin target probes and detection probes. 1. 18S-T7 hairpin probe-ligation-Exo; 2. 18S-Univ-CA probe-ligation-Exo; 3. 18S-double strand T7-ligation; 4. T7 hairpin probe; 5. Univ-CA-probe.
FIG. 19 illustrate steps of single tube assay for isothermal amplification of RNA. Single tube isothermal assay-reverse transcription-ligation-/n vitro transcription (IVT) for RNA detection. 1. (maize-18S-rRNA probe+maize total RNA) RT+T7 double strand promoter no ligase; 2. (maize-18S-rRNA probe+maize total RNA) RT+T7 double strand promoter-ligation-IVT; 3. (maize-18S-rRNA probe+maize total RNA) RT+T7 double strand promoter-ligation.

Results: RNA sequence difference can be distinguished by the target hairpin probe and adding one of the four nucleotides (FIG. 17).

Example 7

Single Tube Isothermal Assay (RT-Ligation) for RNA Detection

RT reaction and ligation reaction was done in a single tube. The reaction containing 1 μl SNP2-Template-RNA (25 μM), and 1.5 μl RHG-SNP2-probe-C (50 μM), was denatured by heating the reaction at 95° C. for 5 min followed by annealing (option) and adding 2.5 μl RT mix [0.5 μl DTT (0.1 M), 1 μl 5× First Strand Buffer, 0.25 μl dXTP (5 mM), 0.25 μl M-MLV Reverse Transcriptase (200 u/μl), 0.5 μl H$_2$O], well mix by pipetting up and down and then a 10 μl ligation mix [0.8 μl T4 DNA ligase (3 U/μl), 1.5 μl 10× T4 ligation buffer, 1.0 μl Univ-CA (50 μM), 6.7 μl water] was added. The reaction was performed at 37° C. for 20 min. Followed this reaction, 1 μl Exonuclease (ExoI: ExoIII=1:1) was added and incubated at 37° C. for 3 hr to remove linear RNA and DNA molecules.

Results: RNA sequence difference can be distinguished by the target hairpin probe and adding one of the four nucleotides (FIG. 18).

Example 8

Single Tube Isothermal Assay for RNA Detection with In Vitro Transcription of Ligated Products after RT and Ligation Reaction For this experiment, synthetic sense and antisense linear double stranded detection probe with T7 promoter sequences were used for this assay.

```
Sense strand (T7-reverse-primer)
5'-PHOS/CTCCCTATAGTGAGTCGTATTA-3'      (SEQ ID NO: 30)

Antisense strand (T7-forward-primer)
5'-TAATACGACTCACTATAGGGAGCA-3'         (SEQ ID NO: 31)
```

Mix of equal amount T7-reverse-primer T7-forward-primer and heated at 95° C. for 3 min, and annealing at 37° C. to produce a "T7-double-strand-promoter". The reaction containing 0.25 µl maize total RNA (0.5 µg/µl), and 1.5 µl 18S-rRNA-probe-G or 28S-rRNA-probe-G (50 µM), 2.5 µl RT mix [0.5 µl DTT (0.1 M), 5× First Strand Buffer, 0.25 µl dXTP (5 mM, Invitrogen), 0.25 µM-MLV Reverse Transcriptase (200 u/µl, Invitrogen), 0.5 µl $H_2O$], well mix by pipetting up and down and then a 10 µl ligation mix [0.8 µl T4 DNA ligase (3 U/µl, Promega), 1.5 µl 10× T4 ligation buffer, 1.0 µl double strand T7-promoter or T7-hairpin-3 (50 µM), 6.7 µl water] was added. Well mix, and then 15 µl IVT mix [5×IVT buffer mix with NTP (ABI) 6 µl, T7-RNA polymerase (ABI) 0.75 pyrophophase (ABI) 0.75 Rnase H 0.75 µl, DEPC-Water 6.75 µl] The reaction was performed at 37° C. for 2 hr.

The above teachings are intended to illustrate the invention and do not by their details limit the scope of the claims of the invention. While preferred illustrative embodiments of the present invention are described, it will be apparent to one skilled in the art that various changes and modifications may be made therein without departing from the invention, and it is intended in the appended claims to cover all such changes and modifications that fall within the true spirit and scope of the invention.

What is claimed is:

1. A method of detecting the presence of a target sequence in a polynucleotide analyte contained in a sample, comprising:
   (a) contacting a sample containing an unamplified polynucleotide analyte with a single-stranded DNA target probe having a sequence capable of hybridizing with a target sequence in the polynucleotide analyte, under conditions effective to form a double-stranded complex between the polynucleotide analyte and the single-stranded DNA target probe, wherein the single-stranded DNA target probe has a hairpin structure;
   (b) incubating the double-stranded complex in the presence of a polymerase and no more than three kinds of nucleotide triphosphates, wherein a selected one or more target-directed nucleotide bases is added to the single-stranded DNA target probe's 3' end to produce a modified single-stranded DNA target probe having a hairpin structure and a 3' sticky end;
   (c) hybridizing the modified single-stranded DNA target probe with a single-stranded DNA detection probe, wherein the single-stranded DNA detection probe (i) does not hybridize to the target sequence in the polynucleotide analyte, (ii) does not ligate with the unmodified single-stranded DNA target probe, and (iii) has a hairpin structure with a 3' sticky end complementary to the 3' sticky end of the modified single-stranded DNA target probe;
   (d) ligating the modified single-stranded DNA target probe and the single-stranded DNA detection probe to form a circular two-probe ligation product, wherein the polynucleotide analyte is not used as a template to form the circular two-probe ligation product;
   (e) after formation of the circular two-probe ligation product, degrading linear nucleic acid molecules;
   (f) amplifying the circular two-probe ligation product to produce a detectable amplicon; and
   (g) detecting the presence of the circular two-probe ligation product by detecting the amplicon.

2. The method of claim 1, wherein said step (b) includes the additional step of dissociating the modified single-stranded DNA target probe from the polynucleotide analyte by denaturation or degrading the polynucleotide analyte.

3. The method of claim 1, wherein the modified single-stranded DNA target probe has a sticky end consisting of one to three nucleotides.

4. The method of claim 1, wherein the amount of the single-stranded DNA target probe in said step (a) is in substantial molar excess of the amount of the polynucleotide analyte, and which further includes repeating said steps (a) and (b) to increase the amount of modified single-stranded DNA target probe present in the sample, and said repeating steps (a) and (b) includes heating the sample after each step (b) to release the modified single-stranded DNA target probe from the polynucleotide analyte, and cooling the sample as part of each step (a) to hybridize unreacted single-stranded DNA target probe with said target sequence.

5. The method of claim 1, for use in detecting a target region of interest in the polynucleotide analyte, wherein said single-stranded DNA target probe has a 3'-end nucleotide base that hybridizes to a base in the target sequence immediately adjacent the target region of interest, and wherein said step (b) is carried out so the 3'-end sequence of the modified single-stranded DNA target probe is produced to identify the target region of interest.

6. The method of claim 1, for use in detecting a plurality of target sequences of interest in one or more polynucleotides in a sample, wherein in said step (a) the sample is mixed with a plurality of single-stranded DNA target probes, each single-stranded DNA target probe having a hairpin structure and a sequence capable of hybridizing with one of said plurality of target sequences, wherein said step (c) includes adding one or more single-stranded DNA detection probes, and wherein the method further comprises dividing the circular two-probe ligation products into two or more sample aliquots and detecting the circular two-probe ligation products in each sample aliquot.

7. The method of claim 6, wherein detecting the circular two-probe ligation products comprises hybridizing amplicons amplified from the circular two-probe ligation products with probes attached on solid surfaces.

8. The method of claim 6, wherein said plurality of single-stranded DNA target probes is synthesized on a solid surface in a reaction vessel, and is released from the solid surface to form a mixture comprising the plurality of single-stranded DNA target probes.

9. The method of claim 1, wherein one of the single-stranded DNA target probe or single-stranded DNA detection probe is attached to a support, the circular two-probe ligation product produced in said step (d) is also attached to the support, and said method includes detecting the presence of the circular two-probe ligation product on the support.

10. A method for detecting a non-polynucleotide analyte, the method comprising:
    attaching a polynucleotide target sequence to the non-polynucleotide analyte; and
    detecting the attached polynucleotide target sequence by a method comprising:
    (a) contacting the polynucleotide target sequence with a single-stranded DNA target probe having a sequence capable of hybridizing with the polynucleotide target sequence, under conditions effective to form a double-stranded complex between the polynucleotide target sequence and the single-stranded DNA target probe, wherein the single-stranded DNA target probe has a hairpin structure;
    (b) incubating the double-stranded complex in the presence of a polymerase and no more than three kinds of nucleotide triphosphates, wherein a selected one or more target-directed nucleotide bases is added to the single-stranded DNA target probe's 3' end to produce a modified single-stranded DNA target probe having a hairpin structure and a 3' sticky end;
    (c) hybridizing the modified single-stranded DNA target probe with a single-stranded DNA detection probe, wherein the single-stranded DNA detection probe (i) does not hybridize to the polynucleotide target sequence, (ii) does not ligate with the unmodified single-stranded DNA target probe, and (iii) has a hairpin structure with a 3' sticky end complementary to the 3' sticky end of the modified single-stranded DNA target probe;
    (d) ligating the modified single-stranded DNA target probe and the single-stranded DNA detection probe to form a circular two-probe ligation product, wherein the polynucleotide target sequence is not used as a template to form the circular two-probe ligation product;
    (e) after formation of the circular two-probe ligation product, degrading linear nucleic acid molecules;
    (f) amplifying the circular two-probe ligation product to produce a detectable amplicon; and
    (g) detecting the presence of the circular two-probe ligation product by detecting the amplicon,
    thereby detecting the presence of the non-polynucleotide analyte.

11. The method of claim 1, wherein said polynucleotide analyte is an RNA polynucleotide analyte and the polymerase is a reverse transcriptase polymerase.

12. The method of claim 11, wherein said step (b) includes degrading the RNA polynucleotide analyte after or during formation of the modified single-stranded DNA target probe.

13. The method of claim 11, wherein the amount of the single-stranded DNA target probe in said step (a) is in substantial molar excess of the amount of the RNA polynucleotide analyte, and which further includes repeating said steps (a) and (b) to increase the amount of modified single-stranded DNA probe present in the sample, wherein repeating said steps (a) and (b) includes heating the sample after each step (b) to release the modified single-stranded DNA probe from the RNA polynucleotide analyte, and cooling the sample as part of each step (a) to hybridize unreacted single-stranded DNA target probe with said RNA polynucleotide analyte.

14. The method of claim 11, wherein said circular two-probe ligation product produced in step (d) contains a promoter sequence, wherein amplifying said circular two-probe ligation product includes reacting the circular two-probe ligation product with a promoter-dependent polymerase under conditions effective to promote synthesis of transcripts containing the single-stranded DNA target probe sequence, and wherein detecting the presence of the circular two-probe ligation product comprises detecting the presence of the transcripts.

15. The method of claim 14, wherein detecting the presence of the transcripts containing the single-stranded DNA target probe sequence includes reacting the transcripts with molecular beacon probes contained in the reaction medium used to generate the transcripts.

16. The method of claim 14, which further includes repeating said steps (a)-(g), where the RNA polynucleotide analyte in repeated step (a) is supplied by said transcripts containing the single-stranded DNA target probe sequence.

17. The method of claim 10, wherein the non-polynucleotide analyte is a polypeptide.

18. The method of claim 17, wherein the polypeptide is an antibody.

19. The method of claim 18, wherein the antibody is bound to an antigen.

20. The method of claim 19, wherein a plurality of antigens are bound by a plurality of antibodies; wherein each antibody is specific to a particular antigen;
    further wherein a plurality of different polynucleotide target sequences are attached to the antibodies such that each polynucleotide target sequence is specific to a particular antibody; and
    further wherein a plurality of different single-stranded DNA target probes are used such that each single-stranded DNA target probe is specific to a particular polynucleotide target sequence.

21. The method of claim 1, wherein the sample is a cell lysate.

22. The method of claim 1, wherein the polynucleotide analyte is genomic DNA.

23. The method of claim 1, wherein the double-stranded complex of step (b) is incubated in the presence of a polymerase and a single kind of nucleotide triphosphate.

24. The method of claim 3, wherein the modified single-stranded DNA target probe has a sticky end consisting of two nucleotides.

25. The method of claim 1, wherein steps (a)-(d) are performed within a single reaction vessel.

26. The method of claim 1, wherein the method is performed within a single reaction vessel.

27. A method of detecting the presence of a target sequence in a polynucleotide analyte contained in a sample, comprising:
(a) contacting a sample containing an unamplified polynucleotide analyte with a single-stranded DNA target probe having a sequence capable of hybridizing with a target sequence in the polynucleotide analyte, under conditions effective to form a double-stranded complex between the polynucleotide analyte and the single-stranded DNA target probe, wherein the amount of single-stranded DNA target probe is in substantial molar excess of the amount of the polynucleotide analyte, and wherein the single-stranded DNA target probe has a hairpin structure;
(b) incubating the double-stranded complex in the presence of a polymerase and no more than three kinds of nucleotide triphosphates, wherein a selected one or more target-directed nucleotide bases is added to the single-stranded DNA target probe's 3' end to produce a modified single-stranded DNA target probe having a hairpin structure and a 3' sticky end;
(c) repeating steps (a) and (b) to increase the amount of modified single-stranded DNA target probe present in the sample, wherein said repeating includes heating the sample after each step (b) to release modified single-stranded DNA target probe from the polynucleotide analyte and cooling the sample as part of each step (a) to hybridize unreacted single-stranded DNA target probe with said target sequence;
(d) hybridizing the modified single-stranded DNA target probe with a single-stranded DNA detection probe, wherein the single-stranded DNA detection probe (i) does not hybridize to the target sequence in the polynucleotide analyte, (ii) does not ligate with the unmodified single-stranded DNA target probe, and (iii) has a hairpin structure with a 3' sticky end complementary to the 3' sticky end of the modified single-stranded DNA target probe;
(e) ligating the modified single-stranded DNA target probe and the single-stranded DNA detection probe to form a circular two-probe ligation product, wherein the ligation reaction does not use the polynucleotide analyte as a template to form the circular two-probe ligation product, and
(f) detecting the presence of the circular two-probe ligation product.

28. The method of claim 27, wherein detecting the presence of the circular two-probe ligation product comprises degrading any linear nucleic acid molecules remaining after formation of the circular two-probe ligation product.

29. The method of claim 28, wherein detecting the presence of the circular two-probe ligation product further comprises amplifying the circular two-probe ligation product to produce a detectable amplicon.

* * * * *